(12) United States Patent
Kang

(10) Patent No.: US 7,115,258 B2
(45) Date of Patent: *Oct. 3, 2006

(54) VESICULAR MONOAMINE TRANSPORTER GENE THERAPY IN PARKINSON'S DISEASE

(75) Inventor: Un Jung Kang, Northbrook, IL (US)

(73) Assignee: Arch Development Corp., Chicago, IL (US)

( * ) Notice: Subject to any disclaimer, the term of this patent is extended or adjusted under 35 U.S.C. 154(b) by 362 days.

This patent is subject to a terminal disclaimer.

(21) Appl. No.: 10/285,308

(22) Filed: Oct. 31, 2002

(65) Prior Publication Data

US 2003/0143702 A1    Jul. 31, 2003

Related U.S. Application Data

(63) Continuation of application No. 09/461,793, filed on Dec. 15, 1999, now Pat. No. 6,506,378.

(60) Provisional application No. 60/112,502, filed on Dec. 16, 1998.

(51) Int. Cl.
| | |
|---|---|
| A01N 63/00 | (2006.01) |
| A01N 43/04 | (2006.01) |
| C12P 21/06 | (2006.01) |
| C12N 5/00 | (2006.01) |
| C12N 15/00 | (2006.01) |
| C12N 15/63 | (2006.01) |

(52) U.S. Cl. ................. 424/93.21; 424/93.1; 424/93.2; 435/69.1; 435/320.1; 435/325; 435/455; 514/44

(58) Field of Classification Search ............... 424/93.1, 424/93.2, 93.21; 435/69.1, 320.1, 325, 455; 514/44

See application file for complete search history.

(56) References Cited

U.S. PATENT DOCUMENTS

| | | | |
|---|---|---|---|
| 4,419,446 A | 12/1983 | Howley et al. ............... 435/68 |
| 4,663,349 A | 5/1987 | Repta .......................... 514/535 |
| 4,758,571 A | 7/1988 | Curtius et al. .............. 514/258 |
| 4,771,073 A | 9/1988 | Repta .......................... 514/535 |
| 4,826,875 A | 5/1989 | Cheisi ........................ 514/534 |
| 4,863,962 A | 9/1989 | Karoum et al. ............. 514/561 |
| 4,873,263 A | 10/1989 | Repta .......................... 514/535 |
| 4,970,200 A | 11/1990 | Birkmayer et al. ........... 514/52 |
| 5,017,607 A | 5/1991 | Chiesi ......................... 514/534 |
| 5,112,861 A | 5/1992 | Backstrom et al. ......... 514/520 |
| 5,135,956 A | 8/1992 | Borg et al. .................. 514/724 |
| 5,206,226 A | 4/1993 | Sabin ........................... 514/75 |
| 5,210,076 A | 5/1993 | Berliner et al. ............... 514/21 |
| 5,565,460 A | 10/1996 | Suzuki et al. .............. 514/259 |
| 5,576,353 A | 11/1996 | Youdim et al. ............. 514/647 |
| 5,587,378 A | 12/1996 | Suzuki et al. .............. 514/264 |
| 5,607,969 A | 3/1997 | Milman et al. ............. 514/538 |
| 5,624,820 A | 4/1997 | Cooper ....................... 435/69.1 |
| 5,650,443 A | 7/1997 | Johnson et al. ............. 514/626 |
| 5,658,900 A | 8/1997 | Boireau et al. ............. 514/217 |
| 5,674,703 A | 10/1997 | Woo et al. .................. 435/69.1 |
| 5,674,885 A | 10/1997 | Boireau et al. ............. 514/367 |
| 5,677,344 A | 10/1997 | Greenfield et al. ......... 514/592 |
| 5,686,423 A | 11/1997 | Wang et al. .................. 514/18 |
| 5,703,100 A | 12/1997 | McDonald et al. ......... 514/343 |
| 5,712,270 A | 1/1998 | Sabb ........................... 514/212 |
| 5,756,548 A | 5/1998 | Flitter et al. ................ 514/616 |
| 5,756,550 A | 5/1998 | Johnson et al. ............. 514/626 |
| 5,807,871 A | 9/1998 | Moltzen et al. ............. 514/323 |
| 5,817,491 A | 10/1998 | Yee et al. ................. 435/172.3 |
| 5,817,690 A | 10/1998 | Mewshaw .................... 514/418 |
| 5,817,699 A | 10/1998 | Flores et al. ................ 514/647 |
| 6,103,226 A * | 8/2000 | Kang et al. ............... 424/93.21 |
| 6,506,378 B1 * | 1/2003 | Kang ....................... 424/93.21 |

FOREIGN PATENT DOCUMENTS

EP    0123456 A2 *   1/2000   ................. 100/100

OTHER PUBLICATIONS

Juengst BMJ, 326:1410-11, 2003.*
Rosenberg et al, Science 287:1751, 2000.*
Friedmann, Science 287(5461):2163-5, 2000.*
Verma et al Nature 389:239-242, 1997.*
Touchette, Nat. Med. 2(1) 7-8, 1996.*
Howard Nat Biotech 21:1117-1118, 2003.*
Bankiewicz et al. Experimental Neurology, 144:147-I56, 1997.*
Bjorklund et al Nature Neuroscience, 3:537-544, 2000.*
Burton et al Gene Therapy 10:1721-177, 2003.*
Erickson et al PNAS 93:5166-5171, 1996.*
Nirenberg et al J. Neurosci, 16:4135-4145, 1996.*
Check Nature 422:7, 2003.*
Lee et al, Vesicular monoamine transporter-2 and aromatic L-amino acid decarboxylase enhance dopamine delivery after L-3, 4-dihydroxyphenylalanine administration in Parkinsonian rats. J Neurosci. 19(8):3266-74, 1999.*
Eck et al., "Gene-based therapy." Goodman & Gilman's The Pharmacological Basis of Therapeutics, McGraw-Hill-Nith Edition: 77-101, 1996.*

(Continued)

*Primary Examiner*—Sumesh Kaushal
(74) *Attorney, Agent, or Firm*—Alice O. Martin; Barnes & Thornburg LLP

(57) ABSTRACT

The present invention provides methods and compositions for the therapeutic intervention of Parkinson's disease. More particularly, methods of making and sequestering dopamine are disclosed. Additionally, methods of genetically modifying donor cells by gene transfer for grafting into the central nervous system to treat defective, diseased or damaged cells are disclosed. Methods and compositions for carrying out such gene transfer and grafting are described.

6 Claims, 5 Drawing Sheets

OTHER PUBLICATIONS

Raymon et al., "Application of ex Vivo Gene Therapy in the Treatment of Parkinson's Disease." Exp. Neurology, vol. 144 : 82-91, 1997.*

Horellou et al., "Gene Therapy for Parkinson's Disease." Molecular Neurobiol., vol. 15: 241-256, 1997.*

Bankiewicz et al., "Practical Aspects of the Development of ex Vivo and in Vivo Gene Therapy for Parkinson's Disease." Exp. Neurology, vol. 144: 147-156, 1997.*

Sanberg et al., "Cellular therapeutic approaches for neurodegenerative disorders." Proceedings of the 1998 Miami Bio/Tech. Winter Symposium, Nucleic acids symposium series No. 38, pp. 139-142, Feb. 1998.*

Scheffler et al., "Marrow-mindedness : a perspective on neuropoiesis." TINS, vol. 22 (8): 348-357, 1999.*

Orkin et al., "Report and recommendations of the panel to assess the NIH investment in research on gene theapy." pp. 1-20, Dec. 1995.*

Bartlett et al., "Efficient expression of protein coding genes from the murine U1 small nuclear RNA promoters," Proc. Natl. Acad. Sci. USA, 93:8852-8857, 1996.

Bencsics et al., "Double transduction with GTP cyclohydrolase I and tyrosine hydroxylase is necessary for spontaneous synthesis of L-DOPA by primary fibroblasts," J. Neurosci. 16, 4449 1996.

Bjorklund and Stenevi, "Intracerebral neural grafting: a historical perspective," in Neural Grafting on the Mammalian CNS, Bjorklund and Stenevi, eds, Amsterdam: Elservier, 3-11, 1985.

Brundin et al., "Intracerebral grafts of neuronal cell suspensions," in Neural Grafting in the Mammalian CNS, Bjorklund and Stenevi, eds., Ch. 6, pp. 51-60, 1985.

Caettano and MacKay, "Proliferation and differentiation of neuronal stem cells regulated by nerve growth factor," Nature 347:762-765, 1990.

Chang et al., "Biochemical and anatomical characterization of forepaw adjusting steps in rat models of Parkinson's disease: studies on medial forebrain bundle and striatal lesions," Neuroscience, 88, 2 617-628, 1999.

Cooper et al., "L-Dopa esters as potential prodrugs: effect on brain concentration of dopamine metabolites in reserpinized mice," J. Pharm. Pharmacol. 39:809-818, 1987.

Das, "Intraparenchymal transplantation," in Neural Grafting in the Mammalian CNS, Bjorklund and Stenevi, eds., Ch. 3 pp. 23-30 1985.

David and Aguayo, "Peripheral nerve transplantation techniques to study axonal regeneration from the CNS of adult mammals," in Neural Grafting in the Mammalian CNS, Bjorklund and Stenevi, eds., Ch. 7, pp. 61-70, 1985.

Erickson and Eiden, "Functional identification and molecular cloning of a human brain vesicle monoamine transporter," J Neurochem. 61(6):2314-2317, 1993.

Erickson et al., "Distinct pharmacological properties and distribution in neurons and endocrine cells of two isoforms of the human vesicular monoamine transporter," Proc Natl Acad Sci USA. 93(10):5166-71, 1996.

Fisher et al., "Survival and function of intrastriatally grafted primary fibroblasts genetically modified to produce L-Dopa," Neuron 6:371-380, 1991.

Fisher, et al., "Transduction with recombinant adeno-virus for gene therapy is limited by leading-strand synthesis," J. Virol., 70(1):520-532, 1996.

Freed, "Transplantation of tissues to the cerebral ventricles: methodological details and rate of graft survival," in Neural Grafting in the Mammalian CNS, Bjorklund and Stenevi, eds., Ch. 4, pp. 31-40, 1985.

Furukawa et al., "GTP-cyclohydrolase I gene mutations in hereditary progressive and dopa-responsive dystonia," Ann. Neurol. 39, 609-617, 1996.

Gasnier et al, "Expression of a bovine vesicular monoamine transporter in COS cells," FEBS Lett. 342, 225 1994.

Hattori et al., "Dendro axionic neurotransmission. II Morphological sites for the synthesis, binding and release of neurotransmitters in dopaminergic dendrites in the substantia nigra and cholinergic dendrites in the neostriatum," Brain Res. 170:71-83, 1979.

Horellou et al., "In vivo release of DOPA and dopamine from genetically engineered cells grafted to denervated rat striatum," Neuron 5:393-402, 1990.

Hoshimaru et al., "Differentiation of the immortalized adult neuronal progenitor cell line HC2S2 into neurons by regulatable suppression of the v-*myc* oncogene," Proc. Natl. Acad. Sci. USA 93, 1518 1996.

Howell et al., "Cloning and functional expression of a tetrabenzine sensitive vesicular monoamine transporter from bovine chromaffin granules," FEBS Lett. 338(1):16-22, 1994.

Ichinose et al., "Heredity progressive dystonia with marked diurnal fluctuation caused by mutations in the GTP cyclohydrolase I gene," Nat. Genet. 8, 236 1994.

Joki, et al., "Activation of the radiosensitive EGR-1 promoter induces expression of the herpes simplex virus thymidine kinase gene and sensitivity of human glioma cells to ganciclovir," Human Gene Ther., 6:1507-1513, 1995.

Juncos et al., "Levodopa methyl ester treatment of Parkinson's disease," Neurology 37:1742-1245, 1987.

Kang et al., "Regulation of dopamine production by genetically modified primary fibroblasts," J. Neurosci. 13(12):5203-5211, 1993.

Lindvall et al., "Transplantation in Parkinson's disease: two cases of adrenal medullary grafts to the putamen," Ann. Neurol. 22:457-468, 1987.

Lindvall et al., "Grafts of fetal dopamine neurons survive and improve motor function in Parkinson's disease," Science 247:574-577, 1990.

Liu et al., "A cDNA that suppresses $MPP^+$ toxicity encodes a vesicular amine transporter," Cell 70:539 1992.

Mandel et al., "Characterization of intrastriatal recombinant adeno-associated virus-mediated gene transfer of human tyrosine hydroxylase and human GTP-cyclohydrolase I in a rat model of Parkinson's disease," J. Neurosci. 18(11):4271-84, 1998.

Mercer et al., "The smooth endoplasmic reticulum as a possible storage site for dendritic dopamine in substantia nigra neurones," Experientia 35:101-103, 1979.

Merickel et al., "Identification of residues involved in substrate recognition by a vesicular monoamine transporter," J. Biol. Chem. 270, 25798 1995.

Misawa et al., "Calcium-independent release of acetylcholine from stable cell lines expressing mouse choline acetyltransferase cDNA," J. Neurochem. 62:465 1994.

Nirenberg et al., "Ultrastructural localization of the vesicular monoamine transporter-2 in midbrain dopaminergic neurons: potential sites for somatodendritic storage and release of dopamine," J. Neurosci. 16, 4135 1996.

Nygaard et al., "Long-term treatment response and fluorodopa positron emission tomographic scanning of Parkinsonism in a family with dopa-responsive dystonia," Ann. Neurol., 32:603-607, 1992.

Olsson et al., "Foerelimb akinesia in the rat Parkinson model: differential effects of dopamine agonists and nigral transplants as assessed by a new stepping test," J. Neurosci., 15:3863-3875, 1995.

Peter et al., "Chromosomal localization of the human vesicular amine transporter genes," Genomics, 18(3):720-3, 1993.

Peter et al., "The chromaffin granule and synaptic vesicle amine transporters differ in substrate recognition and sensitivity to the inhibitors," J Biol Chem. 269(10):7231-7, 1994.

Phillips, "Dynamic aspects of chromaffin granule structure," Neuroscience 7(7):1595-1609, 1982.

Potter et al., "Enhancer-dependent expression of human κ immunoglobulin genes introduced into mouse pre-B lymphocytes by electroporation," Proc. Nat'l Acad. Sci. USA, 81:7161-7165, 1984.

Ruppert et al., "Rat-1 fibroblasts engineered with $GAD_{65}$ and $GAD_{67}$ cDNAs in retroviral vectors produce and release GABA," J. Neurochem. 61:768-771, 1993.

Sawle et al., "Transplantation of fetal dopamine neurons in Parkinson's disease: PET [$^{18}$F]6-L-fluorodopa studies in two patients with putaminal implants," Ann. Neurol., 31:166-173, 1992.

Scherman and Boschi, "Time required for transmitter accumulation inside monoaminergic storage vesicles differs in peripheral and in central systems," *Neuroscience* 27(3):1029-1035, 1988.

Seiger, "Preparation of immature central nervous system regions for transplantation," in *Neural Grafting in the Mammalian CNS*, Bjorklund and Stenevi, eds., Ch. 8, pp. 71-77 1985.

Silva and Bunney, "Intracellular studies of dopamine neurons in vitro: pacemakers modulated by dopamine," *Eur. J. Pharmacol.* 149:307-315, 1988.

Snow et al., "Positron emission tomographic studies of dopa-responsive dystonia and early-onset idiopathic Parkinsonism," *Ann. Neurol.* 34(5):733-738, 1993.

Stenevi et al., "Solid neural grafts in intracerebral transplantation cavities," in *Neural Grafting in the Mammalian CNS*, Bjorklund and Stenevi, eds., Ch. 5, pp. 41-50, 1985.

Sulzer et al., "Reserpine inhibits amphetamine in ventral midbrain culture," *Mol. Pharmacol.* 49, 338 1996.

Surratt et al., Ahuman synaptic vesicle monoamine transporter cDNA predicts posttranslational modifications, reveals chromosome 10 gene localization and identifies *Taq*I RFLPs, *FEBS Lett.* 318(3):325-330, 1993.

Toneguzzo et al., "Electric field-mediated DNA transfer: transient and stable gene expression in human and mouse lymphoid cells," *Molec. Cell. Biol.*, 6(2):703-706, 1986.

Turjanski et al., "Comparison of striatal $^{18}$F-dopa uptake in adult-onset dystonia-parkinsonism, Parkinson's disease, and dopa-responsive dystonia," *Neurology* 43:1563-1568, 1993.

Varoqui and Erickson, "Vesicular neurotransmitter transports," *Mol Neurobiol*.15(2):165-191, 1997.

von Grafenstein et al., "The effect of botulinum toxin type D on the triggered and constitutive exocytosis/endocytosis cycles in cultures of bovine adrenal medullary cells," *FEBS Lett.* 298(2,3):118-122, 1992.

Wachtel et al., "Role of aromatic L-amino acid decarboxylase for dopamine replacement by genetically modified fibroblasts in a rat model of Parkinson's disease," *J. Neurochem.* 69, 2055 1997.

Walther and Stein, "Cell type specific and inducible promoters for vectors in gene therapy as an approach for cell targeting," *J. Mol. Med*, 74:379-392, 1996.

Weihe et al., "Localization of vesicular monoamine transporter isoforms (Vmat1 and Vmat2) to endocrine cells and neurons in rat," *J. Mol. Neuroscien.*, 5:149-164, 1994.

Wictorin et al., "Reformation of long axon pathways in adult rat central nervous system by human forebrain neuroblasts," *Nature*, 347:556-558, 1990.

Wolff et al., "Grafting fibroblasts genetically modified to produce L-Dopa in a rat model of Parkinson's disease," *Proc. Natl. Acad. Sci. USA* 86:9011-9014, 1987.

Horellou and Miller, "Gene therapy for Parkinson's Disease," *Mol. Neurobiol.*, 15(2):241-256, 1997.

Bankiewicz et al., "Practical aspects of the development of *ex vivo* and *in vivo* gene therapy for Parkinson's Disease," *Exper. Neurol.*, 144:147-156, 1997.

Shen et al., "Triple transduction with adeno-associated virus vectors expressing tyrosine hydroxylase, aromatic-L-amino-acid decarboxylase and GTP cyclohydrolase I for gene therapy of Parkinson's Disease," *Human Gene Ther.*, 11:1509-1519, 2000.

Leff et al., "Long-term restoration of striatal L-aromatic amino acid decarboxylase activity using recombinant adeno-associated viral vector gene transfer in a rodent model of Parkinson's Disease," *Neurosci.*, 92(1):185-196, 1999.

Mandel et al., "Characterization of intrastriatal recombinant adeno-associated virus-mediated gene transfer of human tyrosine hydroxylase and human GTP-cyclohydrolase I in a rat model of Parkinson's Disease," *J. Neurosci.*, 18(11):4271-4284, 1998.

Olsson et al., "Forelimb akinesia in the rat Parkinson model: differential effects of dopamine agonists and nigral transplants as assessed by a new stepping test," *J. Neurosci.*, 15(5):3863-3875, 1995.

Winkler et al., "Short-term GDNF treatment provides long-term rescue of lesioned nigral dopaminergic neurons in a rat model Parkinson's Disease," *J. Neurosci.*, 16(22):7206-7215, 1996.

Kirik et al., "Characterization of behavioral and neurodegenerative changes following partial lesions of the nigrostriatal dopamine system induced by intrastriatal 6-hydroxydopamine in the rat," *Exper. Neurol.*, 152:259-277, 1998.

Baker et al., "Simultaneous intrastriatal and intranigral dopaminergic grafts in Parkinsonian rat model: role of intranigral graft," *J. Comp. Neurol.*, 426:106-116, 2000.

Barneoud et al., "Evaluation of simple and complex sensorimotor behaviours in rats with a partial lesion of the dopaminergic nigrostaiatal system," *J. Neurosci.*, 12:322-336, 2000.

Kirik et al., "Long-term rAAV-mediated gene transfer of GDNF in the rat Parkinson's model: intrastriatal but not intranigral transduction promotes functional regeneration in the lesioned nigrostriatal system," *J. Neurosci.*, 20(12):4686-4700, 2000.

Bjorklund and Lindvall, "Cell replacement therapies for central nervous system disorders," *Nature Neurosci.*, 3(6):537-544, 2000.

Imaoka et al., "Significant behavioral recovery in Parkinson's Disease model by direct intracerebral gene transfer using continuous injection of a plasmid DNA-liposome complex," *Hum. Gene Ther.*, 9:1093-1102, 1998.

Fan et al., "Behavioral recovery in 6-hydroxydopamine-lesioned rats by cotransduction of striatum with tyrosine hydroxylase and aromatic L-amino acid decarboxylase genes using two separate adeno-associated virus vectors," *Hum. Gene Ther.*, 9:2527-2535, 1998.

* cited by examiner

FIG. 2A
FIG. 2C
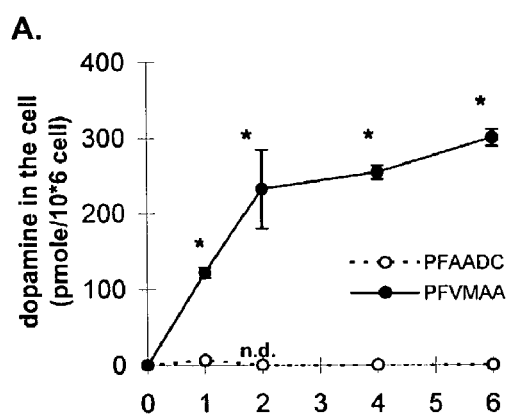
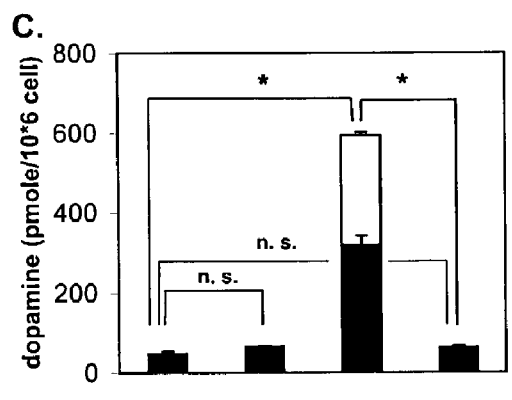
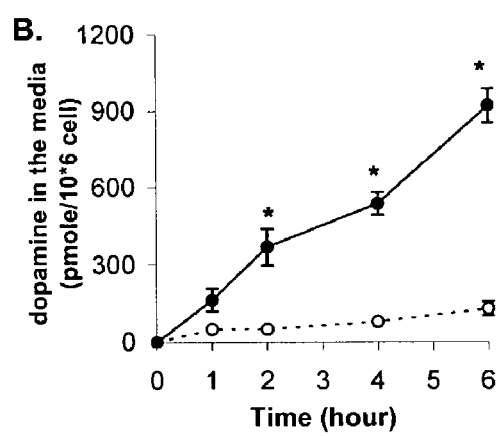
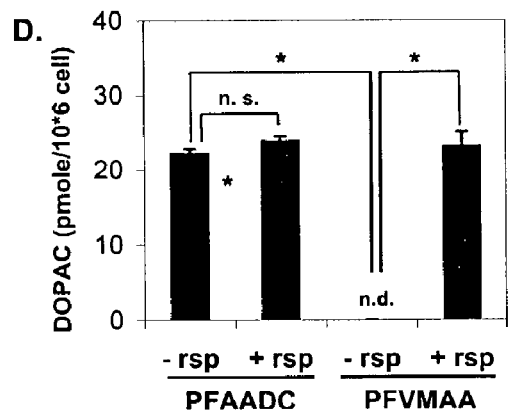
FIG. 2B
FIG. 2D

VESICULAR MONOAMINE TRANSPORTER GENE THERAPY IN PARKINSON'S DISEASE

The present application claims the benefit of U.S. Provisional Patent Application, Ser. No. 60/112,502 filed Dec. 16, 1998 and is a continuation of U.S. Ser. No. 09/461,793 filed Dec. 15, 1999 now U.S. Pat. No. 6,506,378.

The government owns rights in the present invention pursuant to grant number NS32080 from the National Institutes of Health.

BACKGROUND OF THE INVENTION

1. Field of the Invention

The present invention relates generally to the fields of neurobiology and biochemistry. More particularly, it concerns methods and compositions for therapeutic intervention against Parkinson's disease. In particular, methods of making and sequestering dopamine are disclosed.

2. Description of Related Art

Parkinson's disease (PD) is an age-related disorder characterized by a loss of dopamine neurons in the substantia nigra of the midbrain. These neurons have the basal ganglia as their major target organ. The symptoms of PD include tremor, rigidity and ataxia. The disease is progressive, but can be treated by replacement of dopamine through the administration of pharmacological doses of the precursor for dopamine, L-3,4-dihydroxyphenylalanine (levodopa; L-DOPA; Marsden, 1986; Vinken et al., 1986). However, with chronic use of this pharmacotherapy, the patients often develop a fluctuating response to L-DOPA. There are many suggested mechanisms for the development of the fluctuation, but one simple explanation is that the patients reach a threshold of cell and terminal loss, wherein the remaining cells cannot synthesize and store sufficient dopamine from the precursor.

Typically PD patients are routinely treated with a combination of L-DOPA and a DOPA decarboxylase inhibitor such as carbidopa or benserazide. Unfortunately, after an initial period of satisfactory, smooth and stable clinical benefit from L-DOPA therapy, lasting on the average 2–5 years, the condition of many patients deteriorates and they develop complex dose-related, as well as unpredictable, response fluctuations. The causes of the response fluctuations are probably multiple and complex, but pharmacokinetic problems likely play some role. There is a correlation between the clinical fluctuations and the oscillations of L-DOPA plasma levels. However, many of the problems are a result of the unfavorable pharmacodynamics response to L-DOPA, i.e., a short half-life in vivo due to various central factors.

Another treatment route is through intracerebral grafting. PD is the first disease of the brain for which therapeutic intracerebral grafting has been used in humans. Preclinical and clinical data indicate that transplanted cells (the graft) used in cell transplantation protocols for these types of neurodegenerative diseases survive and integrate with the host tissue, and provides functional recovery (Wictorin et al., 1990).

Several attempts have been made to provide the neurotransmitter dopamine to cells of the basal ganglia of Parkinson's patients by transplantation of fetal brain cells from the substantia nigra, an area of the brain rich in dopamine-containing cell bodies and also the area of the brain most affected in PD. Fetal dopaminergic neurons have been shown to be effective in reversing the behavioral deficits in rat models of PD induced by selective dopaminergic neurotoxins (Bjorklund et al., 1986; Dunnett et al., 1983). The major effect of fetal transplantation in PD has been in enhancing patients' response to L-DOPA, rather than alleviating the need for the drug. This effect is thought to be due to added capacity to decarboxylate L-DOPA and storage of the formed dopamine (Lindvall et al, 1994; Sawle et al, 1992).

Non-fetal cell transplants also have been used in an attempt to combat PD, e.g., the use of chromaffin cells. A major advantage of this type of transplantation protocol is that the graft source is not a fetal source and thus, circumvents the ethical and logistical problems associated with acquiring fetal tissue. Using the chromaffin cell protocol, normalization of behavior has been observed. However, the functional recovery of this behavior is temporary and the animals revert to their pre-transplantation status (Bjorklund and Stenevi, 1985; Lindvall et al., 1987). The inability of this type of treatment protocol to maintain normal behavioral activity in animals in the PD model renders clinical application of this protocol as well as other treatment therapies ineffective.

Finally, it is known that the chemical deficit that results in PD is the inability to supply dopamine. The rate limiting enzyme in the production of dopamine, tyrosine hydroxylase, has been cloned and the anatomical localization of the affected region has been identified as the basal ganglia. Nevertheless, in animal models, it has been shown that increasing the activity of tyrosine hydroxylase in Parkinsonian tissue does not result in the long-term amelioration of the symptoms of PD.

Clearly, there is a need for methods and compositions that will correct the chemical deficit in PD in a reliable manner that will lead to the treatment of the disease.

SUMMARY OF THE INVENTION

The present invention provides a method for producing dopamine in a cell comprising transforming a cell with a first polynucleotide encoding aromatic L-amino acid decarboxylase (AADC) and a second polynucleotide encoding vesicular monoamine transporter (VMAT) under conditions suitable for the expression of AADC and VMAT, wherein the polynucleotides each are under the transcriptional control of a promoter active in eukaryotic cells; and contacting the cell with L-3,4-dihydroxyphenylalanine (L-DOPA), whereby AADC converts L-DOPA to dopamine and VMAT sequesters the dopamine in endosomes in the cell. In certain preferred embodiments, the first and second polynucleotides are covalently attached. It is contemplated that the first and second polynucleotides are part of a viral vector. In alternative embodiments, first and second polynucleotides are not covalently attached. It may be that the first and second polynucleotides are part of first and second viral vectors, respectively. It is contemplated that the viral vector may be selected from the group consisting of retrovirus, adenovirus, herpes virus, adeno-associated virus and lentivirus.

In those embodiments in which the first and second polynucleotides are covalently attached it is contemplated that the first and second polynucleotides may be under control of different promoters or under the control of the same promoter. In those embodiments in which the first and second polynucleotides are under the control of the same promoter, the first and second polynucleotides may be separated by an internal ribosome entry site.

It is contemplated that as used herein the promoter may be a tissue specific promoter, an inducible promoter or a constitutive promoter. Such promoters are described throughout the application and are well known to those of skill in the art. In particularly preferred embodiments, the promoter may be selected from the group consisting of CMV IE, SV40 IE, β-actin, EF1-α, a TH promoter, AADC non-neuronal promoter; an AADC promoter, a VMAT2 promoter region, a GTP cyclohydrolase I promoter and a dopamine transporter promoter. Of course these and the other promoters listed throughout the specification are exemplary promoters and one of skill in the art may well substitute other promoter regions for those listed herein and still achieve the objectives of the present invention.

In those embodiments in which the first and second polynucleotides are covalently linked, it is contemplated that the first and second polynucleotides each are covalently linked to a polyadenylation signal.

In particularly preferred embodiments, the cell is a fibroblast cell. In other embodiments the cell may be a fetal brain cell, astrocytes, neuronal stem cells, neuronal precursor cells, myoblasts, bone marrow stromal cells.

In certain aspects of the present invention, it is contemplated that the method further may comprise transforming the cell with a polynucleotide encoding tyrosine hydroxylase (TH) wherein the TH encoding polynucleotide is under the transcriptional control of a promoter. In still further embodiments, the method further may comprise transforming the cell with a polynucleotide encoding GTP cyclohydrolase I (GTPCH) in addition to the polynucleotide encoding TH, wherein the GTPCH polynucleotide is are under the transcriptional control of a promoter.

In specific embodiments, the cell may be transformed in vivo. In other embodiments, the cell is transformed ex vivo and implanted into a subject. In those embodiments in which the cell is implanted into a subject, the L-DOPA may be administered to the patient using any route commonly recommended by a physician. More particularly, it is contemplated that the L-DOPA may be administered orally, subcutaneously or sublingually. In certain defined embodiments, the cell is derived from the subject prior to transformation.

Another aspect of the present invention contemplates a method of treating Parkinson's disease in a subject comprising obtaining a cells from the subject; transforming the cells with a first polynucleotide encoding L-amino acid decarboxylase (AADC) and a second polynucleotide encoding VMAT under conditions suitable for the expression of AADC and VMAT, wherein the polynucleotides each are under the transcriptional control of a promoter; implanting transformed cells into the subject; and providing L-DOPA to the subject, whereby AADC converts L-DOPA in vivo to dopamine and VMAT sequesters the dopamine in endosomes in the cell, which sequestered dopamine over a longer duration of time than from cells without storage of L-DOPA. In particularly preferred embodiments, the L-DOPA is administered orally, sublingually, subcutaneously, intravenously or by duodenal infusion.

It is contemplated that the dose of L-DOPA to be administered may fall within the range of any L-DOPA therapy currently in use or any concentration that becomes useful in future. It is particularly contemplated that the L-DOPA is administered in a dose of between about 50 mg to about 2500 mg of L-DOPA per day. Thus it is contemplated that 50 mg, 75 mg, 100 mg, 250 mg, 300 mg, 350 mg, 400 mg, 450 mg, 500 mg, 550 mg, 600 mg, control of a promoter. In still further embodiments, the method further may comprise transforming the cell with a polynucleotide encoding GTP cyclohydrolase I (GTPCH) in addition to the polynucleotide encoding TH, wherein the GTPCH polynucleotide is are under the transcriptional control of a promoter.

In specific embodiments, the cell may be transformed in vivo. In other embodiments, the cell is transformed ex vivo and implanted into a subject. In those embodiments in which the cell is implanted into a subject, the L-DOPA may be administered to the patient using any route commonly recommended by a physician. More particularly, it is contemplated that the L-DOPA may be administered orally, subcutaneously or sublingually. In certain defined embodiments, the cell is derived from the subject prior to transformation.

Another aspect of the present invention contemplates a method of treating Parkinson's disease in a subject comprising obtaining a cells from the subject; transforming the cells with a first polynucleotide encoding L-amino acid decarboxylase (AADC) and a second polynucleotide encoding VMAT under conditions suitable for the expression of AADC and VMAT, wherein the polynucleotides each are under the transcriptional control of a promoter; implanting transformed cells into the subject; and providing L-DOPA to the subject, whereby AADC converts L-DOPA in vivo to dopamine and VMAT sequesters the dopamine in endosomes in the cell, which sequestered dopamine over a longer duration of time than from cells without storage of L-DOPA. In particularly preferred embodiments, the L-DOPA is administered orally, sublingually, subcutaneously, intravenously or by duodenal infusion.

It is contemplated that the dose of L-DOPA to be administered may fall within the range of any L-DOPA therapy currently in use or any concentration that becomes useful in future. It is particularly contemplated that the L-DOPA is administered in a dose of between about 50 mg to about 2500 mg of L-DOPA per day. Thus it is contemplated that 50 mg, 75 mg, 100 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1250 mg, 1300 mg, 1400 mg, 1500 mg, 1600 mg, 1700 mg, 1800 mg, 1900 mg, 2000 mg, 2100 mg, 2200 mg, 2300 mg 2400 mg, 2500 mg of L-DOPA per day or more. This dose of L-DOPA may be administered in one dose or alternatively may be split into several (2, 3, 4, 5 or more) aliquots to be administered over the period of 24 hours. Alternatively, it also is contemplated that the L-DOPA may be administered continuously throughout the day. It is contemplated that the L-DOPA is administered alone or alternatively may be administered in combination with carbidopa and/or any other PD therapeutic agent as described in the specification below. In particularly preferred embodiments, the L-DOPA is administered in combination with carbidopa at a dose of between about 20 mg to about 300 mg carbidopa per day. Thus it is contemplated that 20 mg, 30 mg, 40 mg, 50 mg, 60 mg, 70 mg, 80 mg, 90 mg, 100 mg, 110 mg, 120 mg, 130 mg, 140 mg, 150 mg 160 mg, 170 mg, 180 mg 190 mg, 200 mg, 210 mg, 220 mg, 230 mg, 240 mg, 250 mg, 260 mg, 270 mg, 280 mg, 290 mg, 300 mg carbidopa per day or more may be administered. This may be administered in a single dose or in multiple doses throughout the day.

In specific embodiments, it is contemplated that the transformed cells are implanted via stereostaxic surgery.

Also contemplated by the present invention is a kit comprising a polynucleotide encoding aromatic L-amino acid decarboxylase (AADC); and a polynucleotide encoding vesicular monoamine transporter (VMAT), the polynucleotides being located in suitable container means therefor.

In preferred embodiments, the VMAT is VMAT type II. In other preferred embodiments, the VMAT is VMAT type I. In specifically defined embodiments, the polynucleotides each are part of a viral vector and each are under the transcriptional control of a promoter active in eukaryotic cells. In particular embodiments, the viral vector is selected from the group consisting of retrovirus, adenovirus, herpes virus, adeno-associated virus and lentivirus. In certain preferred embodiments the-kit comprises L-DOPA in a suitable container means therefor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A–FIG. 2D. Dopamine production and storage in genetically modified fibroblast cells from exogenous L-DOPA. Time course of intracellular (FIG. 2A) and extracellular (FIG. 2B) dopamine levels in PFAADC cells (open circle) and PFVMAA cells (solid circle) after 1 μM L-DOPA incubation for various duration (0 to 6 hours). The dopamine (FIG. 2C) and DOPAC (FIG. 2D) levels in PFAADC cells and PFVMAA cells after 2 hour-incubation with 1 μM L-DOPA and 3 μM reserpine (+rsp) or without reserpine (−rsp). The catecholamine levels were measured both in the media (solid bar) and in the cells (open bar). Data represent the mean±SEM (n=3), from a representative set of several experiments. n.d., nondetectable levels. * $p<0.01$, Newman-Keuls post-hoc analysis.

(FIG. 3A) Time course of dopamine release from PFVMAA cells that were preincubated with 1 μM of L-DOPA for 2 hours to store dopamine (intracellular: open bar). After pre-incubation, the media was replaced with fresh media without L-DOPA and dopamine levels in the media (solid bar) were measured at one hour intervals. (FIG. 3B) The dopamine levels in the media (solid bar) and in the cell pellets (open bars) of PFVMAA cells in different calcium conditions. Cells were preincubated with 1 μM L-DOPA in the media for 3 hours, which were replaced with fresh physiological media (control), physiological media with 20 μM A23187 (Sigma), or by calcium-free media with 10 mM EGTA for 20 minutes of further incubation. Data represent the mean±SEM (n=3). n.d., nondetectable levels. n.s., no significant, * $p<0.01$, Student t-test analysis.

(FIG. 4D) Time course of the contralateral forepaw adjusting steps after L-DOPA administration (6 mg/kg). Data represent the mean±SEM (n=6 for PF, n=8 for PFAADC, n=11 for PFVMAA). † $p<0.05$, * $p<0.01$ relative to pre-L-DOPA step numbers by Newman-Keuls post-hoc analysis. Benserazide was given at 25 mg/kg i.p. in all groups for both biochemical and behavioral measures.

FIG. 5E and FIG. 5F show example of VMAT-2 immunohistochemistry and d shows Nissl staining. The grafts contained PF (FIG. 5A and FIG. 5D), PFAADC (FIG. 5B and FIG. 5E), or PFVMAA (FIG. 5C and FIG. 5F) cells. The scale bar equals 500 μm.

DESCRIPTION OF ILLUSTRATIVE EMBODIMENTS

Figure 1A:
FIG. 1A–FIG. 1F. Transgene expression in genetically modified fibroblasts. The top row (FIG. 1A to FIG. 1C) shows examples of AADC immunohistochemistry. Both PFAADC (FIG. 1B) and PFVMAA (FIG. 1C) show immunoreactivity to AADC antibody. The bottom row (FIG. 1D to FIG. 1F) shows example of VMAT-2 immunohistochemistry. Only PFVMAA (FIG. 1F) shows immunoreactivity to VMAT-2 especially in perinuclear area. PF (FIG. 1A and FIG. 1D) does not show any immunoreactivity to AADC or VMAT-2 antibody. The scale bar equals 500 μm.
Figure 1B:
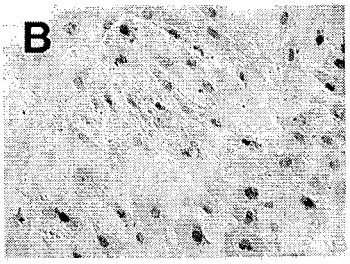
Figure 1C:
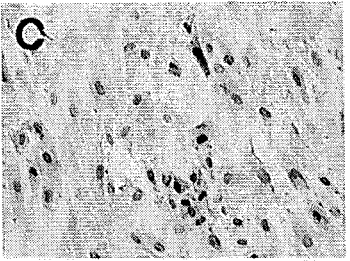
Figure 1D:
Figure 1E:
Figure 1F:
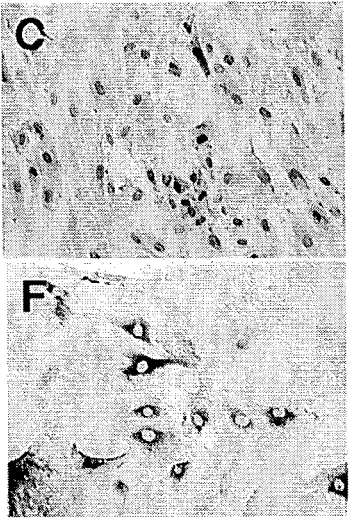

PD is a slowly progressive disease that affects the dopaminergic neurons in the substantia nigra of the brain. Gradual degeneration of these cells causes a reduction in dopamine. This decrease in dopamine can produce one or more of the classic signs of PD. This neurological syndrome is manifested by the combination of resting tremor (or trembling) of the arms and legs, stiffness and rigidity, loss of postural reflexes, and slowness of movement. Other symptoms observed in some persons with PD can include, small cramped handwriting (micrographia); lack of arm swing on the affected side; decreased facial expression (hypomimia); lowered voice volume (dysarthria); feelings of depression or anxiety; episodes of being "stuck in place" when initiating a step . . . called "freezing"; slight foot drag on the affected side; increase in dandruff or oily skin; less frequent blinking and swallowing.

There have been numerous attempts to treat PD patients. All such attempts are based around the correction of the biochemical deficit that manifests in PD, i.e., the inability to supply dopamine. PD patients have been routinely treated with a combination of L-DOPA and a DOPA decarboxylase inhibitor such as carbidopa or benserazide. Unfortunately, patients develop fluctuating responses to such treatment after long term therapy. Additional therapies have attempted to graft cells to the brain of affected patients. The source of these cells has primarily been the fetus. In most cases, providing such grafts merely increases the PD patient's response to the L-DOPA provided as opposed to alleviating the need for the drug. There are a few examples of patients who improved dramatically and did not require any medication. However, the difficulty in obtaining proper donor tissues in sufficient amounts renders clinical application of this protocol premature.

Thus, short duration and fluctuating responses limit the efficacy of L-DOPA therapy for PD. The loss of dopamine storage capacity is thought to be primarily responsible for development of such complications. Although PD cannot be prevented, individualized treatment may result in the amelioration of the symptoms of PD, so that the afflicted individual can live a complete and active life. The present invention is directed at methods and compositions for affecting such a beneficial outcome.

1. The Present Invention

The present invention circumvents the ethical and logistical problems plaguing PD therapy by providing primary fibroblasts that have been genetically modified to produce and store dopamine. Transplanting such cells to a subject animal exhibiting PD restores normal behavior by providing dopamine in an appropriate release from storage vesicles from the transplanted cells. More particularly, the inventor has engineered primary fibroblast cells to express an aromatic L-amino acid decarboxylase in combination with a vesicular monoamine transporter-2 to produce and store dopamine. Grafting these cells in the denervated striatum of Parkinsonian rats prolonged the duration of dopamine elevation and behavioral improvement after exogenous L-DOPA administration.

The advantage of such a gene-based strategy over systemic, current pharmacological methods is in part pharmacokinetics, i e., gene expression is relatively stable leading to consistent production of dopamine and stable striatal levels without the dose fluctuation and alterations in receptor sensitivity and signaling that are observed with oral dosing regimes. Another advantage is that the dopamine production is confined to striatum, avoiding systemic and extrastriatal adverse effects.

Thus, in a broad sense, the present invention provides a method for producing dopamine in a cell. Additional embodiments contemplate methods of treating and or alleviating the symptoms of PD as well as providing kits and compositions for use in such methods. These methods and compositions are described in greater detail herein below.

a. Proteins Involved in Dopamine Production

The biochemical pathway for dopamine production is well characterized. Dopamine is a member of the catecholamine family of neurotransmitters. The catecholamines are derived biosynthetically form L-tyrosine and include dopamine, norephinephrine (noradrenaline) and ephinephrine (adrenaline).

The hydroxylation of L-tyrosine by tyrosine hydroxylase is the first committed step in catecholamine biosynthesis. The action of the hydroxylase yields 3,4,-dihydroxyphenylalanine (L-DOPA). L-DOPA is subsequently decarboxylated by an aromatic L-amino acid decarboxylase (AADC) to produce the human brain neurotransmitter dopamine. Noradrenaline is produced by the hydroxylation of dopamine and noradrenaline is then rearranged to adrenaline. Once neurotransmitters are produced, neurotransmission depends on the regulated release of chemical transmitters molecules. In order for this to happen, once the chemical are synthesized, they are packaged into specialized secretory vesicles of neurons and neuroendocrine cells, a process that is mediated by specific vesicular transporters One such vesicular transporter is vesicular monoamine transporter. Thus, the principle enzymes involved in the synthesis of dopamine are tyrosine hydroxylase and AADC. The present section provides a brief introduction to the proteins involved in the generation and transport of dopamine.

Aromatic L-Amino Acid Decarboxylase.

In order for L-DOPA to bean effective therapeutic for PD, it requires the action of AADC for decarboxylation. This necessity of AADC for dopamine synthesis has been demonstrated previously (Kang et al., 1993). The AADC enzyme has been well characterized from human and other mammalian tissues. Sequences for AADC can be found in Genbank, for example, Genbank Accession No. SEG_HUMAADC0; Genbank Accession No. U31884; Genbank Accession No. SEG_RATAADC; Genbank Accession No. M74029; Genbank Accession No. AF071068; Genbank Accession No. S82290; Genbank Accession No. Z11576; Genbank Accession No. SEG_RATAAADNN; Genbank Accession No. M76180; Genbank Accession No. M58049; Genbank Accession No. SEG_HUMARODE. Each of these sequences is incorporated herein by reference as providing disclosure of AADC protein. Of course it is understood that these are merely exemplary sequences and that sequences variations may also be employed. Methods of generating such variations are well known to those of skill in the art. Additionally, many other AADC proteins may be found in the Genbank database that will be useful in the present invention.

Vesicular Monoamine Transporters.

VMAT1 and VMAT 2 are two isoforms of the vesicular monoamine transporter initially identified using cDNA screening strategies to investigate the passive and active uptake processes in fibroblast cells (Erickson et al., 1992; Liu et al., 1992). Despite the fact that these cells are non-neuroendocrine in nature and lack synaptic vesicles, they do contain endosomes. The initial studies in these cells now provide a convenient in vitro and in situ system for expression and structure analysis of VMAT.

Two separate genes encode VMAT1 and VMAT2. The chromosomal locations of these two genes are 8p21 (Peter et al., 1993) and 10q26.1 (Erickson and Eiden, 1993; Peter et al., 1993; Surratt et al., 1993), respectively. The existence of two genes for the VMAT isoforms suggests that they are differentially expressed in cell type sand impart functionally important differences in vesicular monoamine storage in these cells. VMAT1 is found in adrenal glands and is absent in brain tissue (Lui et al., 1992), whereas VMAT2 is expressed in noradrenergic, dopaminergic and serotonergic cell bodies in the brain stem (Erickson et al., 1992; Lui et al., 1992). For the purposes of the present invention the vesicular monoamine transporter will likely be VMAT2, however, it is contemplated that VMAT1 also may be used.

Sequences for VMAT can be found in Genbank, for example, Genbank Accession No. U39905; Genbank Accession No. AF047575; Genbank Accession No. AA612554; Genbank Accession No. X76380; Genbank Accession No. X71354; Genbank Accession No. L00603; Genbank Accession No. U02876. Each of these sequences is incorporated herein by reference as providing disclosure of VMAT protein. Of course it is understood that these are merely exemplary sequences and that sequences variations may also be employed. Methods of generating such variations are well known to those of skill in the art.

The characteristics of vesicular monoamine transport by VMAT1 and VMAT2 from rat, bovine and human cells have been extensively described in the literature (Erickson et al., 1992; Erickson et al., 1996; Liu et al., 1992; Erickson and Eiden, 1993; Gasnier et al., 1994; Howell et al., 1994; Peter et al., 1994; Weihe et al., 1994). Uptake is energy dependent and the biochemical characteristics of this uptake are well documents (Varoqui and Erickson, 1997).

The cytosolic concentrations of amines in monoaminergic neurons and endocrine cells is estimated to be approximately 10–20 μM (Phillips, 1982; Silva and Bunney, 1988). It is envisioned that the cells of the present invention may be able to produce such concentrations. However, concentrations of about 2 μM dopamine, about 3 μM dopamine, about 4 μM dopamine, about 5 μM dopamine, about 6 μM dopamine, about 7 μM dopamine, about 8 μM dopamine, about 9 μM dopamine, about 11 μM dopamine, about 12 μM dopamine, about 14 μM dopamine, about 16 μM dopamine, about 18 μM dopamine, about 22 μM dopamine, about 24 μM dopamine, about 26 μM dopamine, about 28 μM dopamine, about 30 μM dopamine, or more may be achieved. It is contemplated that the engineered cells of the present invention will secrete dopamine. The concentration of dopamine secreted may vary between batches of cells but will be in the range of 120 pmoles dopamine/$10^6$ cells/hour. This is only an exemplary figure and it is contemplate that the rates of secretion may be 20 pmoles dopamine/$10^6$ cells/hour; 30 pmoles dopamine/$10^6$ cells/hour; 40 pmoles dopamine/$10^6$ cells/hour; 50 pmoles dopamine/$10^6$ cells/hour; 60 pmoles dopamine/$10^6$ cells/hour; 70 pmoles dopamine/$10^6$ cells/hour; 80 pmoles dopamine/$10^6$ cells/hour; 90 pmoles dopamine/$10^6$ cells/hour; 100 pmoles dopamine/$10^6$ cells/hour; 110 pmoles dopamine/$10^6$ cells/hour; 120 pmoles dopamine/$10^6$ cells/hour; 130 pmoles dopamine/$10^6$ cells/hour; 140 pmoles dopamine/$10^6$ cells/hour; 150 pmoles dopamine/$10^6$ cells/hour; 160 pmoles dopamine/$10^6$ cells/hour; 170 pmoles dopamine/$10^6$ cells/hour; 180 pmoles dopamine/$10^6$ cells/hour; 200 pmoles dopamine/$10^6$ cells/hour; 220 pmoles dopamine/$10^6$ cells/hour; 240 pmoles dopamine/$10^6$ cells/hour; 260 pmoles dopamine/$10^6$ cells/hour; 280 pmoles dopamine/$10^6$ cells/hour; 300 pmoles dopamine/$10^6$ cells/hour; 320 pmoles dopamine/$10^6$ cells/hour; 340 pmoles dopamine/$10^6$ cells/hour; 360 pmoles doparine/$10^6$ cells/hour; 380 pmoles dopamine/$10^6$ cells/hour; 400 pmoles dopamine/$10^6$ cells/hour; 450 pmoles dopamine/$10^6$ cells/hour; 500 pmoles dopamine/$10^6$ cells/hour; 650 pmoles dopamine/$10^6$ cells/hour; 700 pmoles dopamine/$10^6$ cells/hour; 750 pmoles dopamine/$10^6$ cells/hour; 800 pmoles dopamine/$10^6$ cells/hour; 850 pmoles dopamine/$10^6$ cells/hour; 900 pmoles dopamine/$10^6$ cells/hour; 1000 pmoles dopamine/$10^6$ cells/hour. Of course it is contemplated that the cells may secrete ranges between any of these figures and may even secrete more than 1000 pmoles dopamine/$10^6$ cells/hour.

A genetically modified population of cells in which the cells have been genetically modified to express an AADC and a VMAT transgene that secretes between about 20 pmoles dopamine/$10^6$ cells/hour and about 1000 pmoles dopamine/$10^6$ cells/hour is one population of cells that will be useful in the present invention. A genetically modified population of cells in which the cells have been genetically modified to express an AADC and a VMAT transgene that secretes between about 40 pmoles dopamine/$10^6$ cells/hour and about 900 pmoles dopamine/$10^6$ cells/hour is one population of cells that will be useful in the present invention. A genetically modified population of cells in which the cells have been genetically modified to express an AADC and a VMAT transgene that secretes between about 60 pmoles dopamine/$10^6$ cells/hour and about 850 pmoles dopamine/$10^6$ cells/hour is one population of cells that will be useful in the present invention. A genetically modified population of cells in which the cells have been genetically modified to express an AADC and a VMAT transgene that secretes between about 80 pmoles dopamine/$10^6$ cells/hour and about 800 pmoles dopamine/$10^6$ cells/hour is one population of cells that will be useful in the present invention. A genetically modified population of cells in which the cells have been genetically modified to express an AADC and a VMAT transgene that secretes between about 100 pmoles dopamine/$10^6$ cells/hour and about 700 pmoles dopamine/$10^6$ cells/hour is one population of cells that will be useful in the present invention. A genetically modified population of cells in which the cells have been genetically modified to express an AADC and a VMAT transgene that secretes between about 150 pmoles dopamine/$10^6$ cells/hour and about 650 pmoles dopamine/$10^6$ cells/hour is one population of cells that will be useful in the present invention. A genetically modified population of cells in which the cells have been genetically modified to express an AADC and a VMAT transgene that secretes between about 200 pmoles dopamine/$10^6$ cells/hour and about 600 pmoles dopamine/$10^6$ cells/hour is one population of cells that will be useful in the present invention. A genetically modified population of cells in which the cells have been genetically modified to express an AADC and a VMAT transgene that secretes between about 250 pmoles dopamine/$10^6$ cells/hour and about 500 pmoles dopamine/$10^6$ cells/hour is one population of cells that will be useful in the present invention. Given the methods and compositions described in the present invention, it will be well within the skill of one in the art to produce populations of cells having various other ranges of dopamine secretion.

The maturation time of monoaminergic vesicles, in terms of time-required to reach steady-state vesicular monoamine accumulation is highly variable being approximately 2 to 4 minutes in the brain, 30 to 60 minutes in the sympathetic nervous system and 30 to 60 hours in the adrenal medullae (Scherman and Boschi, 1988). The reasons for these differences may relate to the presence of different classes of regulated secretory organelles expressing the transporter in endocrine versus neuronal cells.

Using the methods of the present invention, it will be possible to graft cells into subjects exhibiting PD symptoms. These cells will contain the transgenes encoding AADC and a VMAT. The dopamine produced by the action of the AADC will be stored in storage vesicles through the action of the VMAT. Thus the cells will store dopamine in appropriate concentrations, and subsequently release this dopamine in response to the appropriate signals. It is contemplated that the cells may be "loaded" with dopamine before they are grafted into the patient, i.e., the synthesis and storage of the dopamine is allowed to occur in vitro, prior to transplantation. Alternatively, the cells expressing the AADC and VMAT transgenes are transplanted into the appropriate area of the brain and subsequently contacted with L-DOPA in order to affect the in vivo production of dopamine.

Tyrosine Hydroxylase.

Tyrosine Hydroxylase is the rate limiting enzyme in dopamine biosynthesis and is dramatically depleted in the putamen and caudete of Parkinsonian patients and expression of TH and GTP cyclohydrolase I (Bencsics et al., 1996) in the stratium by either ex vivo or in vivo strategies lead to recovery in animal models of the disease. TH and GTP cyclohydrolase I transgene expression in striatal cells, either neuron and/or glia is essentially a biological L-DOPA treatment. The sequence of tyrosine hydroxylase is well known to those of skill in the art. For example, Genbank accession No. AI114408, Y00414, X05290; SEG_HUMTHA0; AF070918; SEG_HUMTHIS0; SEG_HUMTH; D00269; AF030336; AJ000731; AF007942; X76209; Y00414; X05290; X53503; U14395; M17589; M24778. Each of these sequences is incorporated herein by reference as providing disclosure of TH protein. Of course it is understood that these are merely exemplary sequences and that sequences variations may also be employed. Methods of generating such variations are well known to those of skill in the art. Additionally, many other TH proteins may be found in the Genbank database that will be useful in the present invention.

In order to provide L-DOPA into the brain by gene therapy, most studies have focused on the reintroducing TH, with or without GTP cyclohydrolase I, either by direct transfer using viral vectors or by transplanting genetically modified cells (Horellou et al., 1990; Fisher et al., 1991; During et al., 1994; Bencsics el al., 1996; Mandel et al., 1998). In certain embodiments of the present invention, it is envisioned that TH and GTP cyclohydrolase I may be combined with AADC and VMAT to achieve a complete system for the synthesis and sequestering of dopamine.

b. Donor Cells

In any grafting technique, the choice of the donor cells for implantation depends heavily on the nature of the expressed gene, characteristics of the vector and the desired phenotypic result. For example, seeing as retroviral vectors require cell division and DNA synthesis for efficient infection, integration and gene expression (Weiss et al., 1985), if such vectors are used, the donor cells are preferably actively growing cells, such as primary fibroblast culture or established cell lines, replicating embryonic neuronal cells or replicating adult neuronal cells from selected areas such as the olfactory mucosa and possibly developing or reactive glia.

Primary cells, i.e. cells that have been freshly obtained from a subject, such as fibroblasts, that are not in the transformed state are preferred for use in the present invention. Other suitable donor cells include immortalized (transformed cells that continue to divide) fibroblasts, glial cells, adrenal cells, hippocampal cells, keratinocytes, hepatocytes, connective tissue cells, ependymal cells, bone marrow cells, stem cells, leukocytes, chromaffin cells and other mammalian cells susceptible to genetic manipulation and grafting using the methods of the present invention. Additional characteristics of donor cells which are relevant to successful grafting include the age of the donor cells.

Furthermore, there are available methods to induce a state of susceptibility in stationary, non-replicating target cells that will allow many other cell types to be suitable targets for viral transduction. For instance, methods have been developed that permit the successful viral vector infection of primary cultures of adult rat hepatocytes, ordinarily refractory to infection with such vectors, and similar methods may be helpful for a number of other cells (Wolff et al., 1987). In addition, the development of many kinds of vectors derived from herpes, vaccinia, adenovirus, or other viruses, as well as the use of efficient non-viral methods for introducing DNA into donor cells such as electroporation (Toneguzzo et al., 1986), lipofection or direct gene insertion may be used for gene transfer into many other cells. These methods of gene transfer are discussed in further detail elsewhere in the specification.

c. L-DOPA

In particular aspects of the present invention, L-DOPA will be provided to an engineered cell of the present invention. Medicaments and compositions of L-DOPA are well known to those of skill in the art. Such compositions are discussed below, this discussion is not intended to be an exhaustive treatise but rather it is intended to provide examples of such compositions.

Injection of soluble esters of L-DOPA have been proposed as a therapeutic tool for stabilization of patients with severe motor fluctuations following chronic L-DOPA therapy. The L-DOPA methyl ester is one such ester that is likely to be useful in the present invention. U.S. Pat. Nos. 5,017,607; U.S. Pat. 4,826,875; U.S. Pat. 4,873,263; U.S. Pat. 4,663,349; U.S. Pat. 4,771,073; Juncos, et al., (1987) and Cooper, et al., (1987) are incorporated herein by reference as providing disclosure of methods of producing and formulating L-DOPA methyl ester.

Another composition that would be effective in combination with the method of the present invention is L-DOPA ethyl ester. L-DOPA ethyl ester is described in the literature as the hydrochloride salt. The production of L-DOPA ethyl ester is comprehensively discussed in U.S. Pat. No. 5,607,969, incorporated herein by reference.

2. Polynucleotides

The present invention provides methods and compositions of engineering cells to produce and store dopamine. In order to achieve these objectives, the present invention provides transgenes that express an enzyme capable of decarboxylating aromatic amino acids and a transgene that expresses a protein that has vesicular neurotransmitter transport activity. These transgenes comprise polynucleotides that encode AADC, VMAT or any other protein that may be useful in the production and storage of dopamine. Thus these polynucleotides may be inserted into a host cell to produce a donor cell containing that polynucleotide which may, in some cases, be capable of expressing the product of that polynucleotide. In addition to therapeutic considerations, cells expressing polynucleotides of the present invention may prove useful in the context of screening for agents that repress, inhibit, interfere with, block, abrogate, or otherwise ameliorate the PD.

a. Polynucleotides Encoding AADC or VMAT

Polynucleotides used according to the present invention may encode an entire AADC or VMAT gene, a domain, or any other fragment of the protein sequences. Exemplary AADC and VMAT sequences are well known to those of skill in the art and can be found in Genbank as described above. One of skill in the art is referred to the Genbank database which contains various other AADC and VMAT sequences.

As used herein, the term "transgene" means a polynucleotide inserted into a donor cell encoding an amino acid sequence corresponding to a functional protein having some or all of the activity attributed to that particular protein. Such a protein may be a therapeutic protein that is capable of exerting a therapeutic effect on cells of the CNS or having a regulatory effect on the expression of a function in the cells of the CNS.

The polynucleotide may be derived from, genomic DNA, i.e., cloned directly from the genome of a particular organism. In preferred embodiments, however, the polynucleotide would comprise complementary DNA (cDNA). Also contemplated is a cDNA plus a natural intron or an intron derived from another gene; such engineered molecules are sometime referred to as "mini-genes."

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression.

The polynucleotide may be derived from genomic DNA, i.e., cloned directly from the genome of a particular organism. In preferred embodiments, however, the polynucleotide would comprise complementary DNA (cDNA). Also contemplated is a cDNA plus a natural intron or an intron derived from another gene; such engineered molecules are sometime referred to as "mini-genes." At a minimum, these and other polynucleotides of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

Naturally, the present invention also encompasses the use of polynucleotides that are complementary, or essentially complementary, to AADC and VMAT. Polynucleotide sequences that are "complementary" are those that are capable of base-pairing according to the standard Watson-Crick complementary rules. As used herein, the term "complementary sequences" means polynucleotide sequences that are substantially complementary, as may be assessed by the same nucleotide comparison set forth above, or as defined as being capable of hybridizing to AADC or VMAT under relatively stringent conditions such as those described herein. Such sequences may encode the entire AADC or VMAT protein, or functional or non-functional fragments thereof.

It also is contemplated that a given AADC or VMAT from a given species may be represented by natural variants that have slightly different nucleic acid sequences but, nonetheless, encode the same protein. As used in this application, the term "a polynucleotide encoding" refers to a polynucleotide molecule that has been isolated free of total cellular nucleic acid. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

TABLE 1-continued

| Amino Acids | | | Codons |
|---|---|---|---|
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to AADC or VMAT are polynucleotides that may be used in the present invention. Polynucleotides that are essentially the same as AADC or VMAT are also functionally defined as sequences that are capable of hybridizing to a polynucleotide segment containing the complement of AADC or VMAT under standard conditions.

The polynucleotides of the present invention include those encoding biologically functional equivalent AADC or VMAT proteins and peptides. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by humans may be introduced through the application of site-directed mutagenesis techniques or may be introduced randomly and screened later for the desired function, as described below.

b. Oligonucleotide Probes and Primers

In the present invention, an oligonucleotide probe or primer may be utilized which encodes a domain or fragment of AADC or VMAT. A AADC or VMAT probe or primer may be used in a number of molecular biology techniques well known to those skilled in the art including, but not limited to, Southern or Northern blot hybridization, in situ hybridization, or polymerase chain reaction (PCR). One method of exploiting probes and primers of the present invention is in site-directed, or site-specific mutagenesis.

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows for the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. Coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

3. Polypeptides

According to the present invention, AADC or VMAT may act in concert to produce and store dopamine in a genetically engineered cell. While these molecules are structurally distinct, they are part of a pathway involved in the production and release of dopamine and other catecholamine neurotransmitters. In addition to the complete AADC or VMWT molecules, the present invention also relates to fragments of the polypeptides that may or may not retain their respective decarboxylase and transporter activities. Fragments including the N-terminus of the molecule may be generated by genetic engineering of translation stop sites within the coding region. Alternatively, treatment of the AADC or VMAT molecules with proteolytic enzymes, known as protease, can produces a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. One particular fusion of interest would include all or a portion of the native AADC molecule, linked at the N- or C-terminus, to all or a portion of a VMAT polypeptide.

4. Vectors for Cloning, Gene Transfer and Expression

Within certain embodiments, expression vectors are employed to introduce the AADC or VMAT into the host or donor cell. Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells are also defined. The conditions for the use of a number of dominant drug selection markers for establishing permanent, stable cell clones expressing the products are also provided, as is an element that links expression of the drug selection markers to expression of the polypeptide.

a. Regulatory Elements

Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. In certain embodiments, expression includes both transcription of a gene and translation of mRNA into a gene product. In other embodiments, expression only includes transcription of the polynucleotide encoding a gene of interest.

In preferred embodiments, the polynucleotide encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the polynucleotide to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila,* and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline.

In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate.

More particularly, it is contemplated that promoters specific for VMAT and/or AADC as well as TH may be used in the present invention. Such promoters are well known to those of skill in the art. For example, Genbank Accession No. HUMTHC discloses a human TH promoter region, Genbank Accession No. S74903 discloses an AADC non-neuronal promoter; Genbank Accession No. AF023677 discloses a TH promoter; Genbank Accession No. M23597 discloses a tyrosine hydroxylase promoter region; Genbank Accession No. L05074 discloses an AADC promoter region and Genbank Accession No. AF047575 discloses a VMAT2 promoter region. Of course these are only exemplary promoters and any genomic sequences for AADC, VMAT or TH coding genes will contain promoter regions specific for those genes. Genbank Accession Nos. L29478, Z30952 disclose human GTP cyclohydrolase I genes, the promoter region(s) from this and other GTP cyclohydrolase I genes will be particularly useful in the present invention. More particularly, Genbank Accession No. D38603 discloses the promoter region from a *H. sapiens* GTP cyclohydrolase I gene. Another useful promoter will be the promoter from the gene encoding dopamine transporter (see for example the gene sequences; disclosed in Genbank Accession Nos. AF079899; U92262; SEG_HSDOPTRP; U16265; SEG_HUMDATS, each incorporated herein by reference).

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

Tumor specific promoters such as osteocalcin; hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, radiation-inducible (e.g., EGR (Joki et al., 1995)), Alpha-inhibin, RNA pol III tRNA met and other amino acid promoters, U1 snRNA (Bartlett et al., 1996), MC-1, PGK, β-actin and α-globin. Many other promoters that may be useful are listed in Walther and Stein (1996).

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are frequently overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

b. Selectable Markers

In certain embodiments of the invention, the cells contain polynucleotide constructs of the present invention, and a cell may be identified in vitro or in vivo by including a marker in the expression construct. Such markers will confer an identifiable change to the cell permitting easy identification of cells containing the expression construct. Usually the inclusion of a drug selection marker aids in cloning and in the selection of transformants, for example, genes that encode neomycin, puromycin, hygromycin, DHFR, GPT, HPRT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the polynucleotide encoding a gene product. Further examples of selectable markers are well known to one of skill in the art.

c. Multigene Constructs and IRES

In certain embodiments of the invention, internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins, and selectable markers. In this way, expression of several proteins can be simultaneously engineered into a cell with a single construct and a single selectable marker.

5. Introduction of Transgene into a Host Cell

There are a number of ways to introduce expression vectors into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

a. Viral Delivery

Retroviral Vectors.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a polynucleotide encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Lentiviruses can also be used as vectors in the present application. In addition to the long-term expression of the tran-transgene provided by all retroviral vectors, lentiviruses present the opportunity to transduce nondividing cells and potentially achieve regulated expression. The development of lentiviral vectors requires the design of transfer vectors to ferry the transgene with efficient encapsidation of the transgene RNA and with full expression capability, and of a packaging vector to provide packaging machinery in trans but without helper virus production. For both vectors, a knowledge of packaging signal is required-the signal to be included in the transfer vector but excluded from the packaging vector. Exemplary human lentiviruses are human immunodeficiency virus type 1 and type 2 (HIV-1 and HIV-2). HIV-2 is likely better suited for gene transfer than HIV-1 as it is less pathogenic and thus safer during design and production; its desirable nuclear import and undesirable cell-cycle arrest functions are segregated on two separate genes (Arya et al., 1998; Blomer et al., 1997).

Adenoviral Vectors.

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Adeno-associated Viral Vectors.

Adeno-associated virus (AAV) utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map-units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of an AAV vector can be obtained by restriction endonuclease digestion of AAV or a plasmid such as psub201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e. stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicle for gene delivery in vitro, and these vectors are now being developed and tested in pre-clinical and clinical stages for a wide range of applications in potential gene therapy, both ex vivo and in vivo. However, wide variations in AAV transduction efficiency in different cells and tissues in vitro as well as in vivo has been repeatedly observed (Ponnazhagan et al., 1997b; 1997c; 1997d; 1997d) and others (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other Viral Vectors.

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hennonat and Muzycska, 1984) moloney murine leukemia virus (MoMuLV); VSV-G type retroviruses (U.S. Pat. No. 5,817,491, specifically incorporated herein by reference), papovaviruses such as JC, SV40, polyoma (U.S. Pat. No. 5,624,820, specifically incorporated herein by reference) Epstein-Barr Virus (EBV); papilloma viruses (U.S. Pat. No. 5,674,703, specifically incorporated herein by reference), and more particularly, bovine papilloma virus type I (BPV; U.S. Pat. No. 4,419,446, incorporated herein by reference); poliovirus herpesviruses and other human and animal viruses may be employed. These viruses offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up. to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsulated in an infectious viral particle.

b. Non-Viral Delivery

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably integrated into the genome of the cell. This integration may be in the cognate location and orientation via homologous recombination (gene replacement) or it may be integrated in a random, non-specific location (gene augmentation). In yet further embodiments, the polynucleotide may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention, transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. Since these expression constructs have been successfully employed in transfer and expression of polynucleotides in vitro and in vivo, then they are applicable for the present invention. Where a bacterial promoter is employed in the DNA construct, it also will be desirable to include within the liposome an appropriate bacterial polymerase.

Other expression constructs which can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a polynucleotide encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells in vitro, and then the return of the modified cells back into an animal. This may involve the surgical removal of tissue/organs from an animal or the primary culture of cells and tissues.

6. Cellular Grafts

The present section provides a discussion of methods and compositions for grafting donor cells.

a. Preparation of Donor Cells

The donor cells need to be properly prepared for grafting, e.g., for injection of genetically modified donor cells, fibroblasts obtained from for example, skin samples are placed in a suitable culture medium for growth and maintenance of the cells. Such a solution may contain fetal calf serum (FCS) in which the cells are allowed to grow to confluence.

The cells are loosened from the culture substrate for example using a buffered solution containing 0.05% trypsin and placed in a buffered solution such as PBS supplemented with 5% serum to inactivate trypsin. The cells may be washed with PBS using centrifugation and then resuspended in the complete PBS without trypsin and at a selected density for injection. In addition to PBS, any osmotically balanced solution which is physiologically compatible with the host subject may be used to suspend and inject the donor cells into the host.

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the introduced gene product. The mammalian brain has traditionally been considered to be an immunologically privileged organ, but recent work has shown conclusively that immune responses can be demonstrated to foreign antigens in the rat brain. It is important to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life.

The most effective mode and timing of grafting of the transgene donor cells of the invention to treat defects, disease or trauma in the CNS of a patient will depend on the severity of the defect and on the severity and course of disease or injury to cells such as neurons in the CNS, the patient's health and response to treatment and the judgment of the treating health professional.

Of course, as in all other gene-transfer systems, the important issues of appropriate or faithful gene expression must be resolved to ensure that the level of gene expression is sufficient to achieve the desired phenotypic effect and not so high as to be toxic to the cell.

A problem associated with the use of genetically engineered cells as transplants for gene therapy is that as cells become quiescent (non-dividing) the expression of genes, including transgenes, becomes down-regulated (Palmer et al, 1991). Primary fibroblasts grafted into the brain do not continue to divide when implanted unless they are transformed and tumorigenic. They thus exist in a quiescent state in the brain. It is thus useful to provide means for maintaining and/or increasing expression of the transgene in the absence of cell division to promote long term stable expression of therapeutic genes used in fibroblasts for gene therapy.

Expression of a gene is controlled at the transcription, translation or post-translation levels. Transcription initiation is an early and critical event in gene expression. This depends on the promoter and enhancer sequences and is influenced by specific cellular factors that interact with these sequences. The discussion regarding promoters and enhancers above is incorporated herein by reference.

The genetic correction of some, or many, CNS disorders may require the establishment or re-establishment of faithful intercellular synaptic connections. Model systems to study these possibilities have not yet been developed and exploited because of the paucity of replicating non-transformed cell-culture systems and the refractoriness of non-replicating neuronal cells to retroviral infection. However, recent studies, including those involving the immortalization of embryonic hippocampal neuronal cells, suggest that replicating neuronal cell culture systems may soon become available for in vitro gene transfer and then for in vivo implantation (Caettano and MacKay, 1990). Such neurons might be susceptible to efficient transduction by retroviral or other viral vectors, and if they are also able to retain other neuronal characteristics, they may be able to establish synaptic connections with other cells after grafting into the brain. Alternatively, there are cells within the CNS that are late to develop, such as the ventral leaf of the dentate gyrus of the hippocampus, or continue to divide through adulthood, such as those in the olfactory mucosa and in the dentate gyrus. Such cells may be suitable targets for retroviral infection.

The use of non-neuronal cells for grafting may preclude the development of specific neural connections to resident target cells of the host. Therefore, the phenotypic effects of fibroblast or other non-neuronal donor cells or target cells in vivo would be through the diffusion of a required gene product or metabolite, through gap junctions ("metabolic co-operation") or through uptake by target cells of secreted donor cell gene products or metabolites.

Alternatively, neural bridges may be provided which facilitate reconnection between neurons in damaged CNS tissues. As noted above, grafted donor cells suspended in substrate material such as collagen matrices can serve as neural bridges to facilitate axonal regeneration and reconnection of injured neurons, or may be used in conjunction with neural bridges formed from synthetic or biological materials, for example homogenates of neurons or placenta, or neurite promoting extracellular matrices.

b. Grafting Donor Cells

The methods of the invention contemplate intracerebral grafting of donor cells containing a transgene insert to the region of the CNS having sustained defect, disease or trauma. More specifically, the present invention contemplates grafting cells containing AADC/VMAT transgenes to subjects exhibiting PD symptoms.

Neural transplantation or "grafting" involves transplantation of cells into the central nervous system or into the ventricular cavities or subdurally onto the surface of a host brain. Conditions for successful transplantation include: 1) viability of the implant; 2) retention of the graft at the site of transplantation; and 3) minimum amount of pathological reaction at the site of transplantation.

Methods for transplanting various nerve tissues, for example embryonic brain tissue, into host brains have been described in *Neural Grafting in the Mammalian CNS*, Bjorklund and Stenevi, eds., (1985) Das, Ch. 3 pp. 23–30; Freed, Ch 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77 (1985), incorporated by reference herein. These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation (Das, 1985).

The two main procedures for intraparenchymal transplantation are: 1) injecting the donor cells within the host brain parenchyma or 2) preparing a cavity by surgical means to expose the host brain parenchyma and then depositing the graft into the cavity (Das, 1985). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The donor cells may also be introduced into the putamen, nucleus basalis, hippocampus cortex, striatum or caudate regions of the brain, as well as the spinal cord. Preferably, for passaged donor cells, cells are passaged from approximately 2 to approximately 20 passages. Of course it is understood that the cells may be passaged more than 20 times and further it is specifically contemplated that the cells may be passaged 3, 5, 6, 7, 8, 9, 10, 11, 12, 13, 14, 15, 16, 17, 18, 19 or more times.

For grafting, the cell suspension is drawn up into the syringe and administered to anesthetized graft recipients. Multiple injections may be made using this procedure. The age of the donor tissue, i.e. the developmental stage may affect, the success of cell survival after grafting.

The cellular suspension procedure thus permits grafting of genetically modified donor cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^{12}$ cells are introduced per graft. Thus it is envisioned that $10^5$, $10^6$, $10^7$, $10^8$ $10^8$ $10^{10}$ or $10^{11}$ cells may be introduced per graft. Additionally it is contemplated that more than one graft may be necessary, indeed 1, 2, 3, 4, 5, 6, 7, 8, 9, 10 or more grafts may be performed over any given period ranging from days to weeks to months to years.

For transplantation into cavities, which may be preferred for spinal cord grafting, tissue is removed from regions close to the external surface of the CNS to form a transplantation cavity, for example as described by Stenevi et al., (1985), by removing bone overlying the brain and stopping bleeding with a material such a gelfoam. Suction may be used to create the cavity. The graft is then placed in the cavity. More than one transplant may be placed in the same cavity using injection of cells or solid tissue implants.

Grafting of donor cells into a traumatized brain will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

The present invention therefore provides methods for genetically modifying donor cells for grafting CNS to treat defective, diseased and/or injured cells of the CNS.

The methods of the invention also contemplate the use of grafting of transgenic donor cells in combination with other therapeutic procedures to treat disease or trauma in the CNS. Thus, genetically modified donor cells of the invention may be co-grafted with other cells, both genetically modified and non-genetically modified cells which exert beneficial effects on cells in the CNS, such as chromaffin cells from the adrenal gland, fetal brain tissue cells and placental cells. The genetically modified donor cells may thus be supported by the survival and function of co-grafted, non-genetically modified cells.

Moreover, the genetically modified donor cells of the invention may be co-administered with therapeutic agents useful in treating defects, trauma or diseases of the CNS, such as growth factors, erg. nerve growth factor; gangliosides; antibiotics, neurotransmitters, neurohormones, toxins, neurite promoting molecules; and antimetabolites and precursors of these molecules such as the precursor of dopamine, L-DOPA.

C. Tissue Cell Culture

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary (CHO), W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

7. Methods for Screening Active Compounds

The present invention also contemplates the use of the genetically engineered cells of the present invention in the screening of compounds for activity in either stimulating dopamine production, uptake or activity. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, enzyme activity assays in which the decarboxylation or monoamine transport activity is monitored. Additionally, in vivo assays that monitor behavioral traits may be used, such traits include rotational behavior the swing behavior and performance in radial maze tests (see e.g., Ungerstedt et al., 1973; McGurk et al., 1992; U.S. Pat. No. 5,135,956).

a. In vitro Assays

In one embodiment, the invention will be applied to the screening of compounds that bind to the AADC or VMAT proteins or fragments thereof. The polypeptides or fragments may be either free in solution, fixed to a support, or expressed in or on the surface of a cell. Either the polypeptides or the compound may be labeled, thereby permitting a determination of binding. A particularly preferred screening assay is the biochemical screening assay described herein below in Example 4.

In another embodiment, the assay may measure the inhibition of binding of either protein to a natural or artificial substrate or binding partner. Competitive binding assays can be performed in which one of the agents is labeled. Usually, the polypeptide will be the labeled species. One may measure the amount of free label versus bound label to determine binding or inhibition of binding Another technique for high throughput screening of compounds is described in WO 84/03564. Large numbers of small peptide test compounds are synthesized on a solid substrate, such as plastic pins or some other surface. The peptide test compounds are reacted with either protein and washed. Bound polypeptide is detected by various methods.

Purified AADC or VMAT can be coated directly onto plates for use in the aforementioned drug screening techniques. However, non-neutralizing antibodies to the polypeptides can be used to immobilize the polypeptides to a solid phase. Also, fusion proteins containing a reactive region (preferably a terminal region) may be used to link the AADC or VMAT complex active region to a solid phase.

Various cell lines containing wild-type or natural or engineered mutations in the AADC/VMAT combination can be used to study various functional attributes of the proteins and how a candidate compound affects these attributes. Methods for engineering mutations are described elsewhere in this document. In such assays, the compound would be formulated appropriately, given its biochemical nature, and contacted with a target cell. Depending on the assay, culture may be required. The cell may then be examined using a number of different physiologic assays. Alternatively, molecular analysis may be performed in which the function of AADC/VMAT, or related pathways, may be explored. This may involve assays such as those for protein expression, enzyme function, substrate utilization, cAMP levels, mRNA expression (including differential display of whole cell or polyA RNA) and others.

Protein-protein interactions may also be studied by using biochemical techniques such as cross-linking, co-immunoprecipitation, and co-fractionation by chromatography, which are well known to those skilled in the art. The co-immunoprecipitation technique consists of (i) generating a cell lysate; (ii) adding an antibody to the cell lysate; (iii) precipitating and washing the antigen; and (iv) eluting and analyzing the bound proteins (Phizicky and Fields, 1995). The antigen used to generate the antibody can be a purified protein, or a synthetic peptide coupled to a carrier. Both monoclonal and polyclonal antibodies can be utilized in co-immunoprecipitation, or alternatively, a protein can be used which carries an epitope tag recognized by a commercially available antibody.

b. In vivo Assays

Treatment of animals with the engineered cells of the present invention, or test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intracerebral injection.

Determining the effectiveness of a therapy in vivo may involve a variety of different criteria. Such criteria include, but are not limited to, survival, reduction of neurodegeneration, arrest or slowing of PD related tremor, elimination or reduction of other PD related symptoms, increased activity level, improvement in motor skills, improvement in alertness, improvement in sleeping habits, increased energy level, improvement in overall well-being, improvement in immune effector function and improved food intake.

Particularly preferred in vivo assays for determining the effectiveness of the present invention are the behavioral tests described herein below in Example 5. For example, monitoring improvements in deficits in forepaw adjusting steps in models will be a useful tool for investigating the efficacy of therapeutics (Chang et al., 1999). Other behavioral tests well known to those of skill in the art also are contemplated.

8. Methods for Treating Parkinson's Disease

The present invention also involves, in another embodiment, the prevention or treatment of PD in a subject. By treatment, it is intended that the present invention will provide some alleviation of the symptoms of PD. Thus, it is not a requirement that all of the symptoms of PD be removed. Since the cells generated by the present invention have a capacity to produce and sequester dopamine, it is contemplated that grafting such cells into a subject presenting PD will ameliorate some or all of the deleterious effects of PD. Alternatively, the cells of the present invention also may be used to identify additional therapeutic agents that will act to enhance dopamine production and/or release.

The present invention includes, in specific embodiments, methods for the treatment of PD through the delivery of cells expressing functional AADC and VMAT transgenes. These cells will be used for the production and subsequent storage and secretion of dopamine. The L-DOPA that is converted to dopamine may be endogenous to the organism or may be provided from an exogenous source in combination with the genetically modified cells of the present invention.

In many contexts, it is not necessary that all of the symptoms of PD be alleviated. Rather, to accomplish a meaningful treatment, all that is required is that the effects of this neurodegenerative disease be slowed to some degree. It may be either that the cells of the present invention increase the individuals ability to synthesize dopamine, store dopamine or merely provide enough dopamine to alleviate the symptoms of PD. Clinical aspects of PD are well known and defined in the art and include tremor (or trembling) of the arms and legs, stiffness and rigidity, loss of postural reflexes, and slowness of movement as well as other symptoms described above.

a. Genetic Based Therapies

One of the therapeutic embodiments contemplated by the present invention is the intervention, at the molecular level, in events involved in PD. Specifically, the present inventors intend to provide, to a cell or an animal patient, an composition comprising a host cells that. comprises an expression construct capable of producing-AADC and VMAT. Additionally, it is contemplated that a nucleic acid encoding TH and GTP cyclohydrolase I also may be included in the expression construct. Expression of these molecules will provide healthy cells with increased production and/or secretion of the neurotransmitter dopamine. The lengthy discussion of polynucleotides employed herein is incorporated into this section by reference. Particularly preferred polynucleotides are contained in viral vectors such as adenovirus, adeno-associated virus, herpesvirus, vaccinia virus, parvovirus and retrovirus.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the cell. Similar figures may be extrapolated for other non-viral formulations by comparing relative uptake efficiencies.

b. Agents that Alleviate PD

Agents or factors suitable for use in a combined therapy with cell-based therapies of the present invention are any chemical compound or treatment method that alleviates the deleterious effects of PD. Such agents and factors include dopamine, L-DOPA, remacemide, benzamide compounds, levodopa alone or in combination with a DOPA decarboxylase inhibitor such as carbidopa or benserazide. These agents for PD therapy are extensively described in the literature e.g., U.S. Pat. Nos. 5,017,607; U.S. Pat. 4,826,875; U.S. Pat. 4,873,263; U.S. Pat. 4,663,349; U.S. Pat. 4,771,073; U.S. Pat. 5,607,969; U.S. Pat. 5,817,690, 5,817,699, 5,807,871, 5,756,550; 5,756,548. Additional agents known to be useful in the treatment of PD include 2-arylamidothiazole derivatives (U.S. Pat. No. 5,712,270); modulators of acetylcholine receptors (U.S. Pat. No. 5,703,100); peptide mimetic dopamine prodrugs (U.S. Pat. No. 5,686,423); ATP-sensitive potassium channel blocker (U.S. Pat. No. 5,677,344); riluzole (U.S. Pat. No. 5,674,885); carbamazepine and oxcarbazepine (U.S. Pat. No. 5,658,900); remacemide (U.S. Pat. No. 5,650,443); xanthine derivatives (U.S. Pat. No. 5,587,378); N-propargyl-aminoindan compounds (U.S. Pat. No. 5,576,353); therapeutic purine agents (U.S. Pat. No. 5,565,460); nicotinamide adenine dinucleotide agents (U.S. Pat. No. 4,970,200); melanin and melanin-related compounds (U.S. Pat. No. 5,210,076); phytic acid (U.S. Pat. No. 5,206,226); pentanedione derivatives (U.S. Pat. No. 5,112,861); D-DOPA (U.S. Pat. No. 4,863,962); Pterin derivatives (U.S. Pat. No. 4,758,571). Each of these patents is specifically incorporated herein by reference as disclosing compositions that may be used in combination with the therapeutic compositions described in the present invention.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the delivery of AADC/VMAT polynucleotides to patients will be an efficient method for delivering an effective therapy to counteract the effects of the neurodegeneration seen in PD. Similarly, the drugs discussed herein above may be directed to a particular, affected region of the subject's body or be administered systemically.

c. Combined Therapy with Traditional PD Therapies

One goal of current research is to find ways to improve the efficacy of traditional PD therapy. One way is by combining such traditional therapies with gene therapy by grafting cells of the present invention into an animal exhibiting PD symptoms. In the context of the present invention, it is contemplated that the cell-based therapies of the present invention could be used in conjunction with any of the PD therapies described above.

To achieve a therapeutic outcome and alleviate some or all of the symptoms of PD using the methods and compositions of the present invention, one would generally graft the genetically modified donor cell into the brain area of the PD subject and contact said cell or subject at least one other PD therapeutic agent. These compositions would be provided in a combined amount effective to induce an increase in the production, storage and/or secretion of dopamine. This process may involve grafting the genetically cells and providing the agent(s) or factor(s) at the same time. This may be achieved by contacting the PD individual with a single composition or pharmacological formulation that includes both the cellular graft and the additional therapeutic agent(s), or by contacting the PD subject with two distinct compositions or formulations, at the same time, wherein one composition includes the cellular composition and the other includes the agent.

Alternatively, the cell-based treatments may precede or follow the other therapeutic agent treatment by intervals ranging from minutes to weeks. In embodiments where the other agent and the cell-based therapy are applied separately to the PD subject, one would generally ensure that a significant period of time did not expire between the time of each delivery, such that the agent and graft would still be able to exert an advantageously combined effect on the subject. In such instances, it is contemplated that one would contact the subject with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It is also conceivable that more than one administration of either the cellular graft, or the other agent will be desired. Various combinations may be employed, where graft is "A" and the other therapeutic agent is "B", as exemplified below:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated. Again, to achieve a therapeutic outcome, both agents are delivered to a cell in a combined amount effective to increase or enhance the production and/or storage of dopamine.

d. Formulations and Routes for Administration

Where clinical applications are contemplated, it will be necessary to prepare pharmaceutical compositions—expression vectors, cellular grafts, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

In addition to the cellular grafts of the present invention, additional active compositions described herein above present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described above.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can. be brought about by the use in the compositions of agents delaying absorption, for example, aluminum monostearate and gelatin.

9. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture

Fibroblast cells ($2.5 \times 10^5$) were plated in 6 well plates in DMEM media with 10% fetal calf serum with appropriate selection markers as described in (Kang et al., 1993, Bencsics et al., 1996, Wachtel et al., 1997). Catecholamine measurements were done in DMEM media (1 ml in each well) except for the experiments on $Ca^{++}$ effect which were done in physiological incubation medium consisting of 135 mM NaCl, 3 mM KCl, 2 mM $CaCl_2$, 2 mM $MgCl_2$, 10 mM glucose, 200 µM ascorbic acid, and 10 mM HEPES, pH 7.3.

Generate of PFVMAA Cells

A full-length bovine AADC cDNA was cloned into a retroviral vector (LDcSHL; with selection marker hygromycin-B-phosphotransferase under the control of an internal simian virus 40 early promoter) as described (Kang et al., 1993). The 1.6 kilobase fragment containing the full coding lesion and the part of the 3' untranslated lesion of rat VMAT-2 cDNA (a gift from Robert Edwards, University of California, San Francisco, Calif.) was removed by EcoRI, blunted and ligated into LINX (a gift from Fred H. Gage, Salk Biological Institute, La Jolla, Calif., as described by (Hoshimaru et al., 1996) downstream from the $P_{hCMV^*-1}$ promoter. Both were used to generate amphotropic retroviral producer lines from PA317 cells (PAAADC and PAVMAT). Isolation and culture of primaly fibroblast from inbred Fischer 344 rats were described previously (Kang et al., 1993, Benesics et al., 1996, Wachtel et al., 1997). Primary fibroblasts (PF) were infected with either PAAADC or PAVMAT, and selected with hygromycin (150 µg/ml) or G418 (400 µg/ml) to establish PFAADC or PFVMAT cells, respectively. PFAADC was infected with PAVMAT and underwent additional selection in media containing G418 and hygromycin to generate bulk population of primary fibroblast cells expressing both AADC and VMAT-2 (PFVMAA).

Immunostaining Studies

Control and transduced fibroblasts were grown on chamber slide (Lab-Tek), fixed with 4% phosphate-buffered paraformaldehyde, and permeabilized with 0.2% Triton X-100. Cells were immunostained with a rabbit polyclonal antibody against a synthetic peptide at the C terminus of VMAT-2 (Phoenix Pharmaceuticals, Inc., CA) at a dilution of 1:5,000 or a polyclonal antibody against bovine AADC (CA-201 bDCrab, Protos Biotech Corp., NY) at a dilution of 1:1,000, and a biotinylated goat anti-rabbit IgG secondary antibody. The signal was amplified by avidin and biotinylated horseradish peroxidase using the Elite ABC Vectastatin Kit (Vector Labs, CA). VMAT-2 and AADC immunoreactivity were visualized using 3,3'-diaminobenzidine tetrachloride dehydrate (Aldrich Chemical Co., WI) as a chromogen and enhanced by the addition of cobalt chloride/nickel ammonium.

Biochemical Assays

AADC activity was assayed with modification of a $CO_2$ trapping as described, but without using radioactivity (Kang et al., 1993). Supernatant of homogenized cells was added to reaction solution containing 30 mM potassium phosphate buffer, 0.3 mM EDTA, 20 µM pyridoxal 5'-phosphate, and 200 µM L-DOPA. Dopamine levels after reaction were measured by reverse-phase HPLC using a Velosep RP-18 column (100×3.2 mm; Applied Biosystems, Inc., CA) and an ESA Coulochem II electrochemical detector equipped with a 5014 analytical cell. For transporter assay, cells were washed and homogenized as described (Gasnier et al., 1994; Merickel et al., 1995). Cell debris was removed by centrifugation in a microcentrifuge at 4000×g for 5 min. A Bradford assay (Bio-rad) was performed to measure the protein concentration, and supernatant was diluted in SH (sucrose HEPES) buffer to a final concentration of 10 mg/ml. From each transfection, two aliquots were made and frozen at −80° C. An aliquot of frozen membranes was thawed and 20 µl added to 200 µl of SH buffer containing 4 mM KCl, 2.5 mM $MgSO_4$, 2 mM ATP (potassium salt), and 50 nM [$^3$H]serotonin (DuPont NEN) at 29° C. for 5 minutes. The termination of reaction, filtration and radioactivity measurement was performed by the methods as previously described (Gasnier et al., 1994; Merickel et al., 1995). Experiments were performed in triplicates, and background uptake at 0° C. at 0 min was subtracted.

In vivo Studies

The in vivo protocols were approved by the Institutional Animal Care and Use Committee of the University of Chicago. For the dopamine depletion, female Fischer 344 rats (150–200 g) were anesthetized with a mixture of ketamine (75 mg/kg), acepromazine (0.75 mg/kg) and xylazine (3.8 mg/kg). As previously described (Wachtel et al., 1997) for the medial forebrain bundle (MFB) lesion, 8 µg (free base weight) of 6-hydroxydopamine was infused unilaterally in 2 µl at a rate of 0.5 µl/min at the following coordinate: AP −4.4 mm, ML 1.2mm relative to bregma, and −7.5 mm from the dura. Animals with near complete lesions were used for further experiments: rats with more than 400 rotations per hour after D-amphetamine (5 mg/kg, i.p.) administration was used for the microdialysis study and rats with less than 3 forepaw adjusting steps over 12 seconds along 90 cm distance was used for behavioral study. PF, PFAADC, and PFVMAA cell were washed, trypsinized, and suspended in Dulbecco's phosphate-buffered saline. Two microliters of the cell suspension (75,000 cells/µl) was infused at each of four ventral sites (AP 1.2 and −0.3, ML 2.3 and 3.0, DV −4.0) and 1 µl at another four dorsal sites within the same needle tracts (DV −3.5) for a total of 900,000 cells per animal.

Microdialysis

Microdialysis probes were implanted at the center of 4 tracks of grafts (AP 0.45, ML 2.65, DV 5.2) under anesthesia and the microdialysis probes were of vertical concentric design as previously described (Wachtel et al., 1997). Before implantation, the microdialysis probes (2 mm active area) were calibrated in vitro for relative recovery to assure consistency, but the data were not corrected for recovery. Artificial cerebrospinal fluid (147 mM NaCl, 2.5 mM KCl, 1.3 mM $CaCl_2$, and 0.9 mM $MgCl_2$, pH≈7.4) was infused continuously through the probe at a rate of 1.5 µl/min. The day after probe placement, dialysates were collected at 20-min intervals for 340 min after L-DOPA administration in awake, freely moving animals. Twenty microliters of each dialysate sample was analyzed by HPLC for L-DOPA, dopamine, and DOPAC concentrations.

Behavioral Testing

For the behavioral test, we used the coordinates and amount of infused cells optimized to influence forepaw adjusting step with minimal nonspecific effect on the behavior from the graft mass based on our localization of areas in the striatum crucial for the behavior (Olsson et al., 1995). 0.67 µl of the cell suspension (75,000 cells/µl) were infused at each of two VL sites (AP 1.1, ML 3.2, DV 5.7 and 5.0), three VL lateral sites (AP 1.1, ML 4.2, DV 6.0, 5.3, and 4.6), and three VL anterior medial sites (AP 2.2, ML 2.2, DV 5.7, 5.0, and 4.3) for a total of 400,000 cells per animal. The cell suspensions were injected at the rate of 0.5 µl/min using a 10 µl syringe and an infusion pump. Grafting was only done with cells below passage 15. The experimenter holds the rat's hindlimbs and one forepaw, so that the animal must bear its weight solely with its opposing forelimb on the treadmill belt. The number of catch-up steps made while the belt moved 90 cm/12 seconds were counted manually as described (Olsson et al., 1995; Chang et al., 1999). The stepping numbers over five intervals were then averaged for each forepaw. Only rats with complete lesions (from 0 to 3 steps/interval in the contralateral forepaw) were used for experiments. Rats were administered L-DOPA (6 mg/kg) and benserazide (50 mg/kg), and checked for stepping responses at one hour intervals for 6 hours.

Immunohistology

One day after microdialysis and behavioral experiments, rats were anesthetized and transcardially perfused with 125 ml of normal saline followed by 250 ml of ice-cold 4% paraformaldehyde. Brains were removed, postfixed for overnight, and transferred to 30% sucrose until equilibrated. Forty-micrometer sections were cut and stained with Nissl or immunostained with AADC and VMAT-2 antibodies herein.

Example 2

Transgene Expression in Fibroblasts

Primary skin fibroblast cells (PF) from Fischer 344 rats were genetically modified to express AADC (PFAADC) or both VMAT-2 and AADC (PFVMAA) (see Example 1). Expressions of functional transgenes were confirmed by immunohistochemistry and activity assays (FIG. 1A–FIG. 1F and Table 2). The fibroblast cells were incubated with 1 µM L-DOPA, and the dopamine levels both in the cells and media were measured. Previously it has been shown that the control fibroblasts do not produce any detectable dopamine from L-DOPA (Kang et al., 1993). Consistent with previous data, the intracellular storage of dopamine in PFAADC cells were negligible (FIG. 2A) and most of dopamine was released into the extracellular space, increasing with time (FIG. 2B). Extracellular dopamine level in the media of PFVMAA cells also continued to increase with time and was significantly higher than that of PFAADC cells (FIG. 2B). Intracellular dopamine levels in PFVMAA reached a plateau after 2 hours, indicating saturation of the storage capacity for dopamine (FIG. 2A). When fibroblast cells with only VMAT expression were incubated with 1 μM dopamine in the media for an hour, intracellular dopamine levels were 22.5±2.5 pmoles/$10^6$ cells (mean±SEM, n=3) compared to 122.1±6.8 at the same one hour time point in PFVMAA cells (FIG. 2A). Given the fact that both PFVMAA and PFVMAT cells have similar storage capacities (transporter activity of PFV-MAT cells; pmoles 5-HT/mg/5 min), this difference in the dopamine levels indicates that using L-DOPA as a precursor along with AADC for intracellular conversion into dopamine results in much higher levels of dopamine storage than using dopamine itself.

Example 3

Increased Dopamine Production is Due to VMAT-2 Expression

To further demonstrate that the increased dopamine production and storage were due to solely VMAT-2 expression, cells were incubated with L-DOPA (1 μM) and a VMAT inhibitor, reserpine (3 μM) for 2 hours and dopamine levels were measured. Reserpine depleted intracellular dopamine from PFVMAA completely and also decreased extracellular dopamine level of PFVMAA to the levels comparable to that of PFAADC cells (FIG. 2C). Total dopamine production in PFVMAA cells was higher than that in the same cells treated with reserpine or in PFAADC cells (FIG. 2C) despite comparable AADC activities, suggesting that sequestration of the dopamine away from the site of synthesis facilitates total dopamine production. DOPAC was not detected in PFVMAA cells and reserpine treatment of PFVMAA cells increased DOPAC levels to that of PFAADC (FIG. 2D). This is consistent with metabolism of cytoplasmic dopamine by monoamine oxidase (MAO) in PFAADC cells or PFVMAA cells with reserpine. On the other hand, dopamine is protected from the metabolism because it is sequestrated in the vesicles of PFVMAA cells. The lack of metabolism of dopamine contributes to higher total dopamine in PFVMAA, but does not account for the entire difference from other situations noted above. In summary, VMAT-2 not only increases the intracellular storage capacity and reduce metabolism of dopamine, but also increase overall production of dopamine in fibroblasts genetically modified with AADC (see Table 2).

TABLE 2

Activities of recombinant enzymes in genetically modified fibroblasts (n = 3)

|  | PF | PFAADC | PFVMAA |
|---|---|---|---|
| AADC activity (pmole dopamine/mg/min) | 0 | 323.98 (±9.06) | 300.51 (±26.74) |
| VMAT activity (pmole 5-HT/mg/5 min) | 0 | 0 | 48.6 (±12.3) |

Example 4

Dopamine Release from PFVMAA Cells

Figure 3A:
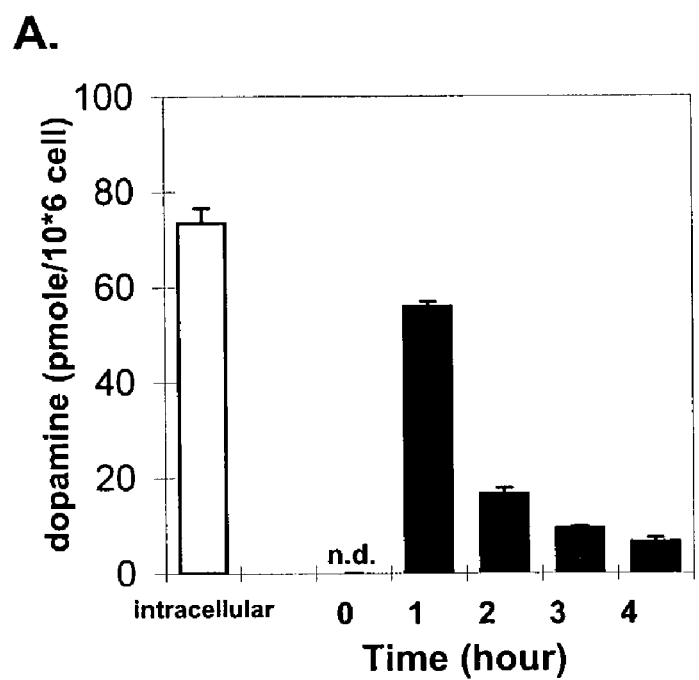
FIG. 3A and FIG. 3B. Release of stored dopamine from PFVMAA.
Figure 3B:
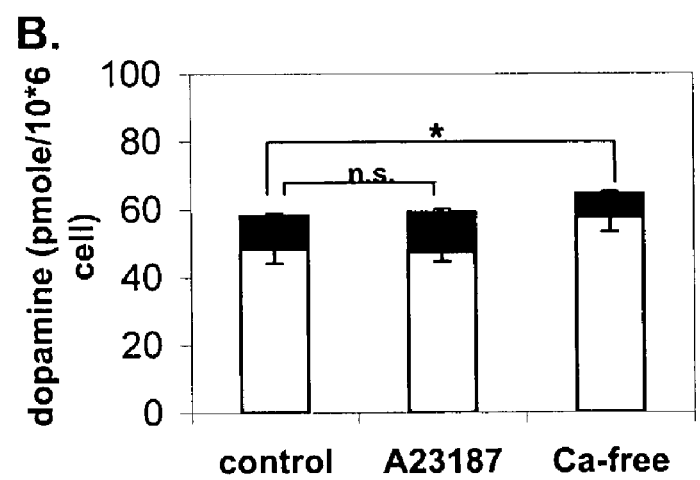

Dopamine stored in PFVMAA cells was released spontaneously and gradually over a few hours in the absence of continuing supply of the precursor L-DOPA (FIG. 3A). Time course of the dopamine release was not performed in PFAADC cells because there was no detectable intracellular dopamine in PFAADC cells after incubation with L-DOPA (FIG. 2A and Kang et al., 1993). To investigate the mechanism of dopamine release in the PFVMAA cells, intracellular calcium was manipulated by using calcium-free media and calcium ionophore. There was significant decrease in dopamine release by calcium depletion and a trend for increased release of dopamine by calcium ionophore (FIG. 3B), suggesting that some of the vesicular release is calcium-dependent. However, the major portion of release was calcium-independent and incubation with high potassium media (40 mM KCl) for 3 minutes did not increase dopamine release. Calcium-independent release of other classic neurotransmitters and peptides from genetically modified fibroblast cells without added storage capacity has been noted previously (Ruppert et al., 1993. Misawa et al., 1994). The majority of dopamine release from PFVMAA is most likely due to constitutive exocytosis of vesicles. VMAT-2 has been found in tubulovesicular organelles of cell bodies and dendrites of dopaminergic neurons (Hattori et al., 1979; Mercer et al., 1979; Nirenberg et al., 1996). Somatodendritic release of dopamine from dopaminergic neurons may occur from this pool of dopamine, in a similar manner as dopamine release from PFVMAA cells. Likewise, $Ca^{++}$-independent constitutive release of catecholamine has been noted in PC-12 cells and chromaffin cells (von Grafenstein et al., 1992; Sulzer et al., 1996).

Example 5

Biochemical Effect of PFVMAA Cell Graft in Parkinsonian Rats

Figure 4A:
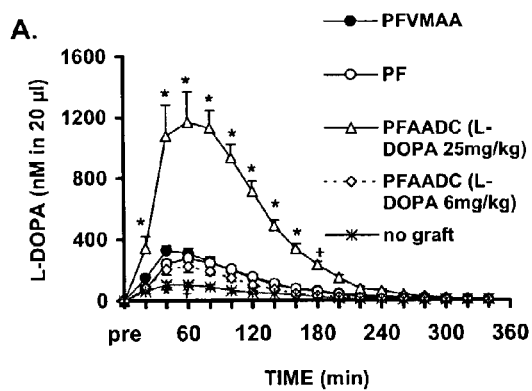
FIG. 4A–FIG. 4D. Time course of biochemical and behavioral changes after L-DOPA injection. Microdialysate concentrations of L-DOPA (FIG. 4A), dopamine (FIG. 4B), DOPAC (FIG. 4C) were measured in 6-OHDA-denervated striatum containing genetically modified grafts at 20 min intervals after L-DOPA i.p. injection (6 mg/kg except for one PFAADC group which received 25 mg/kg). Data represent the mean±SEM (n=3 for no graft control, n=6 for PF, n=4 for PFAADC with 6 mg/kg, n=5 for PFAADC with 25 mg/kg, n=6 for PFVMAA). † $p<0.05$, * $p<0.01$ relative to all other groups in FIG. 4A, relative to AADC 25 mg/kg group in FIG. 4B, relative to PF, no graft, and PFAADC groups given 6 mg/kg of L-DOPA in FIG. 4C, by Newman-Keuls post-hoc analysis.
Figure 4B:
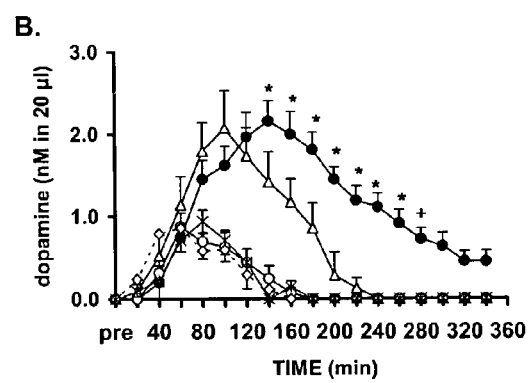
Figure 4C:
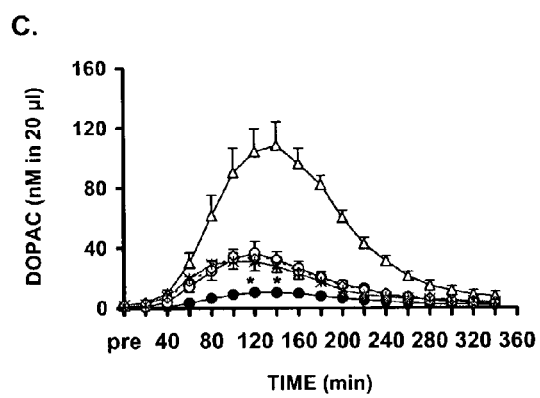

The inventors tested whether PFVMAA cells will prolong the duration of the effect of systemically administered L-DOPA in vivo in terms of dopamine release and behavioral restoration. Rats with unilateral near-complete lesions of nigrostriatal system were produced by injecting 6-hydroxydopamine in the medial forebrain bundle. Grafts were placed in the central area of the striatum along four tracks. Three days later, a microdialysis probe was placed at the center of 4 tracks of grafts and the next day, catecholamine levels were monitored after intraperitoneal administration of L-DOPA and benserazide. AADC gene transfer achieved by the PFAADC cells was not sufficient to increase the dopamine levels produced by the exogenous L-DOPA significantly over the level produced by endogenous AADC in the denervated striatum with the control grafts (FIG. 4A–FIG. 4C). This indicates that the relative contribution of AADC activity provided by the PFAADC grafts is not significant compared to the endogenous capacity to decarboxylate L-DOPA. Significant increases in the level and duration of dopamine elevation were noted in PFVMAA grafted striatum compared to control and PFAADC groups (FIG. 4A–FIG. 4C). To exclude the possibility that the longer duration of dopamine elevation is simply due to a higher peak level, the duration of dopamine elevation in PFAADC group treated was compared with higher dose of L-DOPA (25 mg/kg) that attained the same peak dopamine levels as the PFVMAA group given 6 mg/kg of L-DOPA. The duration of dopamine elevation was significantly longer in PFVMAA group than PFAADC group with higher precursor administration (FIG. 4B). This data is consistent with prolonged dopamine release by PFVMAA cells in addition to increased total dopamine level. Also, it was observed that DOPAC levels were significantly lower in the PFVMAA grafted striatum than all the other groups (FIG. 4C), which is consistent with the fact that VMAT protects dopamine from MAO-mediated metabolism by sequestering it from cytoplasmic space into vesicles.

Example 6

Behavioral Effect of PFVMAA Cell Graft in Parkinsonian Rats

Figure 4D:
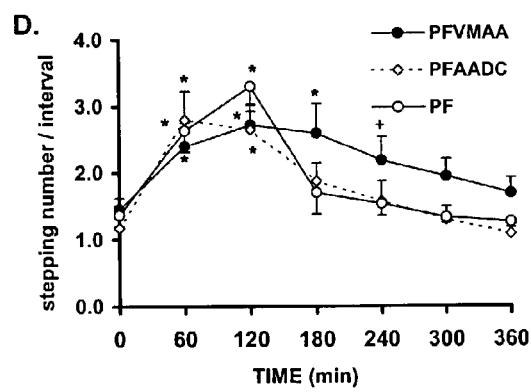
Figures 5A, 5B, 5C, 5D, 5E, 5F, 5G, 5H:
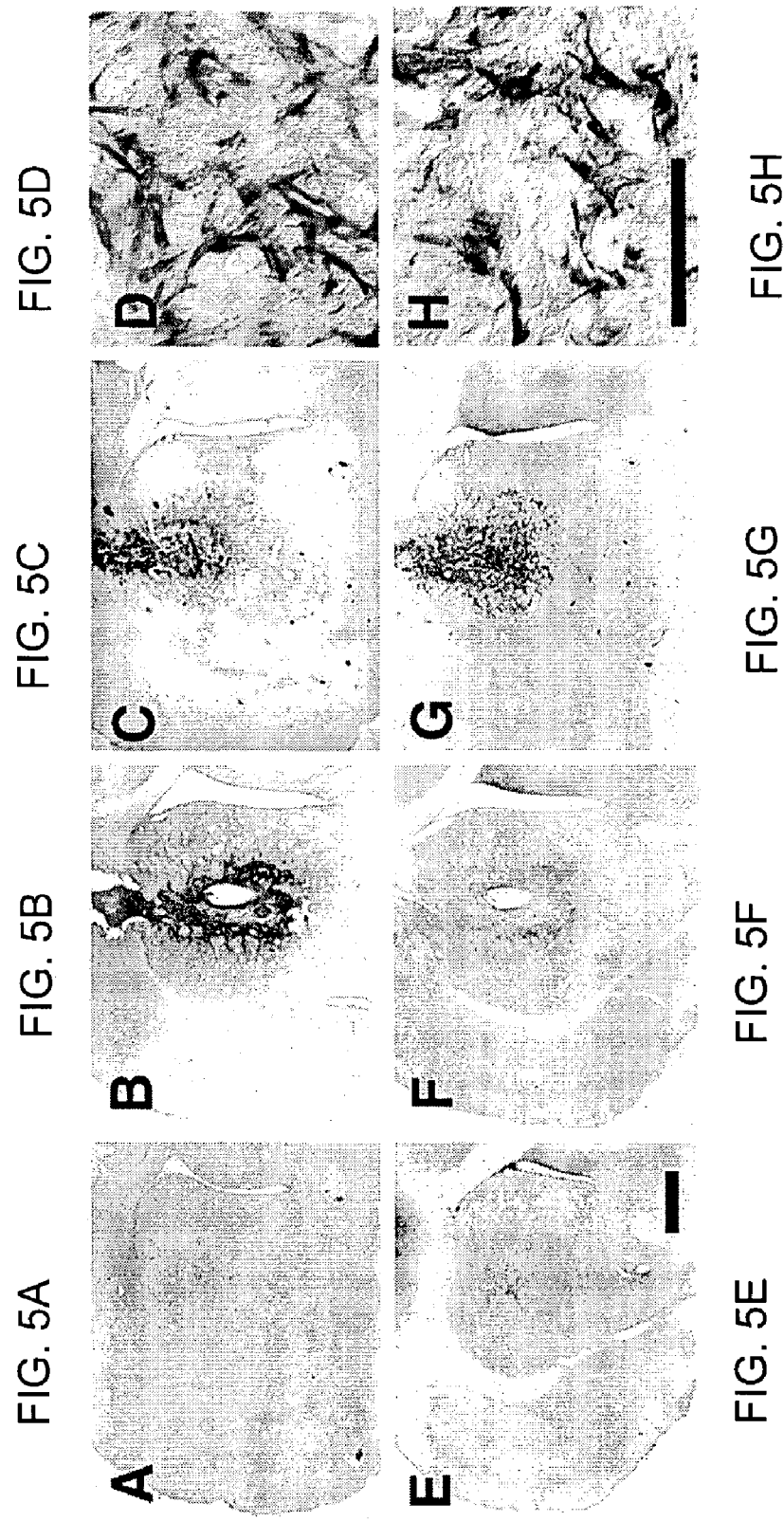
FIG. 5A–FIG. 5H. Immunohistochemical staining of genetically modified grafts in dopamine-denervated striatum (24). The top row (FIG. 5A to FIG. 5C) shows examples of AADC immunohistochemistry. In the bottom row.

To determine whether such prolongation of biochemical effect from grafting PFVMAA cells would also increase the duration of the effect on akinesia of the Parkinsonian rats, the forepaw adjusting steps were utilized as a non-drug-induced behavioral paradigm that reflects dopamine depletion and/or restoration more faithfully than rotational behaviors and reflects akinesia rather than compensatory supersensitive changes (Olsson et al., 1995; Chang et al., 1999). PF, PFAADC, and PFVMAA cells were grafted into denervated striatum and forepaw adjusting steps were monitored for six hours after administration of L-DOPA (6 mg/kg) and benserazide (50 mg/kg) on the seventh day after grafting. Compared to the baseline level before L-DOPA injection, forepaw adjusting steps were significantly elevated for 4 hours in PFVMAA grafted rats, for 2 hours in both PFAADC and PF groups. Again PFAADC did not show significant difference from the control group (FIG. 4D). The genetically modified grafts survived well as noted previously (Bencsics et al., 1996; Wachtel et al., 1997) and expression of transgenes were also confirmed by immunostaining for AADC and VMAT-2 (FIG. 5A–FIG. 5H).

Example 7

Discussion

Addition of storage capacity by VMAT gene transduction significantly increased the peak dopamine levels and duration of its release both in vitro and in vivo from the same dose of L-DOPA. This translated into prolongation of the duration of improvement in akinesia. These findings underline the importance of dopamine storage capacity in the efficacy of L-DOPA therapy. There are clinical examples that underscore the importance of subsequent processing steps of L-DOPA, namely L-DOPA decarboxylation and dopamine storage capacity. DOPA-responsive dystonia is associated with mutations in GTP cyclohydrolase 1 gene that leads to absence of cofactor, tetrahydrobiopterin and consequent lack of dopamine production (Ichinose et al., 1994; Furukawa et al., 1996). Dramatic and smooth response to L-DOPA in these patients is most likely due to their intact L-DOPA decarboxylation and dopamine storage capacity (Nygaard et al., 1992; Snow et al., 1993; Turjanski, et al., 1993). The major effect of fetal transplantation in PD has been in enhancing patients' response to L-DOPA, rather than alleviating the need for the drug and is again likely to be due to added capacity to decarboxylate L-DOPA and store the formed dopamine which has been demonstrated by fluoro-DOPA PET scans (Lindvall et al., 1994; Sawle et al., 1992).

In addition to the prolongation of the effect of L-DOPA to alleviate the short duration response, use of these grafts along with L-DOPA therapy in early to moderate stages of the disease may prevent the development of fluctuations as the PD advances. By allowing a lower dose of L-DOPA to be used in conjunction with the grafts to achieve the same level of dopamine as a higher dose of L-DOPA, it may also reduce side effects that occur due to the diffusion of L-DOPA to other parts of the brain, notably limbic system, such as hallucinations and confusions. Such double gene transduction could be applied to other donor cell types for transplantation including neuronal stem cells as well as to direct in vivo transfer methods using viral vectors such as herpes virus, adenovirus, adeno-associated virus, lentivirus. In addition, genes that are essential for L-DOPA production such as tyrosine hydroxylase and GTP cyclohydrolase 1 (Bencsics et al., 1996) can be combined with AADC and VMAT-2 for production and delivery of dopamine by gene therapy. However, regulation of the optimal levels of dopamine requires additional measures such as use of regulatable promoters. On the other hand, the combination of precursor delivery and AADC/VMAT-2 double gene transduction employed here allows one of skill in the art to regulate the final dopamine delivery by varying the amount of L-DOPA given. In conclusion, key processing steps of L-DOPA outlined herein may lead to successful amelioration of symptoms of PD by improving the major problem of the current mainstay of therapy.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcone, et al., *Nucl. Acids Res.*, 16(8):3195–3207, 1988.
Arya et al., *Hum Gene Ther.*, 9(9):1371–80, 1998
Baichwal and Sugden, In: *Gene Transfer*, Kucherlapati R, ed., New York, Plenum Press, 117–148, 1986.
Bartlett et al., *Proc. Natl. Acad. Sci. USA*, 93:8852–8857, 1996.
Bencsics et al., *J. Neurosci.* 16, 4449 1996.
Benvenisty and Neshif, *Proc. Nat Acad. Sci. USA,* 83:9551–9555, 1986.
Birkmayer et al., *Wien. Klin. Wochenschr.* 73, 787 1961
Bjorklund and Stenevi, eds, in Neural Grafting in the Mammalian CNS, Amsterdam: Elservier, 3–11, 1985.
Bjorklund et al., *Prog Brain Res.* 1986;70:499–512, 1986
Blomer et al., *J Virol.* 71(9):6641–9, 1997
Brundin et al., in *Neural Grafting in the Allammalian CNS*, Bjorklund and Stenevi, eds., Ch. 6, pp. 51–60
Caettano and MacKay, *Nature* 347:762–765, 1990.
Carter and Flotte, *Curr. Top. Microbiol. Immunol.,* 218: 119–144, 1996.
Chang et al. *Biochim Biophys Acta.* 1092(2):153–60, 1991
Chang et al., *Neuroscience,* 88, 2 617–628, 1999
Chatterjee, et al., *Ann. N.Y Acad. Sci.,* 770:79–90, 1995.
Chen and Okayama, *Mol. Cell Biol.,* 7:2745–2752, 1987.
Coffin, In: Fields B N, Knipe D M, ed. Virology. New York: Raven Press, pp. 1437–1500, 1990.
Cooper, et al., *J. Pharm. Pharmacol.* 39:809, 1987

Cotzias, et al., *N. Engl. J. Med.* 276, 374 1967
Couch et al., *Am. Rev. Resp. Dis.*, 88:394–403, 1963.
Coupar et al., *Gene,* 68:1–10,1988.
Das, in *Neural Grafting in the Mammalian CNS*, Bjorklund and Stenevi, eds., Ch. 3 pp. 23–30 1985
David et al., in *Neural Grafting in the Mammalian CNS*, Bjorklund and Stenevi, eds., Ch. 7, pp. 61–70
Dubensky et al., *Proc. Nat. Acad. Sci. USA,* 81:7529–7533, 1984.
Dunnett et al., *Trends Neurosci.* 6:266–270, 1983
Engber et al., *Brain Res.* 581, 261 1992
Erickson and Eiden, *J Neurochem.* 61(6):2314–7, 1993
Erickson et al., Proc Natl Acad Sci USA. 93(10):5166–71, 1996
Erickson et al., *Proc. Natn. Acad. Sci. USA* 89, 10993 1992
Fabbrini et al., *Ann. Neurol.* 21, 370 1987
Fahn, In The scientific basis for the treatment of Parkinson's disease, C. W. Olanow and A. N. Lieberman, Eds. (Canforth, England: Parthenon Publishing Group) p. 89, 1992.
Fechheimer et al., *Proc. Nat'l. Acad. Sci. USA,* 84:8463–8467, 1987.
Ferkol et al., *FASEB J.,* 7:1081–1091, 1993.
Ferrari, et al., *J. Virol.,* 70:3227–3234, 1996.
Fisher et al., *Neuron* 6:371–380, 1991.
Fisher, et al., *J. Virol.,* 70:520–532, 1996.
Flotte, et al., *Proc. Natl. Acad. Sci. USA,* 90:10613–10617, 1993.
Fraley et al., *Proc. Natl. Acad. Sci. USA,* 76:3348–3352, 1979.
Freed, in *Neural Grafting in the Mammalian CNS*, Bjorklund and Stenevi, eds., Ch. 4, pp. 31–40, 1985.
Freshner, In *Animal Cell Culture: a Practical Approach* Second Edition, Oxford/New York, IRL Press, Oxford University Press, 1992.
Friedmann, *Science,* 244:1275–1281, 1989.
Furukawa et al., *Ann. Neurol.* 39, 609 1996.
Gasnier et al., *FEBS Lett.* 342, 225 1994
Gerfen et al., *Science* 250, 1429 1990
Ghosh-Choudhury et al., *EMBO J.,* 6:1733–1739, 1987.
Ghosh and Bachhawat, (Wu G, Wu C ed.), New York: Marcel Dekker, pp.87–104, 1991.
Gnanalingham and Robertson, *Neuroscience* 57, 673 1993.
Gomez-Foix et al., *J. Biol. Chem.,* 267:25129–25134, 1992.
Goodman, et al., *Blood,* 84:1492–1500, 1994.
Gopal, *Mol. Cell Biol,* 5:1188–1190, 1985.
Gossen and Bujard, *Proc. Natl. Acad. Sci. USA,* 89:5547–5551, 1992.
Gossen et al., *Science,* 268:1766–1769, 1995.
Graham and Prevec, *Biotechnology,* 20:363–390, 1992.
Graham and Prevec, In: E. J. Murray (ed.), Methods in Molecular Biology: Gene Transfer and Expression Protocol, Clifton, N.J.: Humana Press, 7:109–128, 1991.
Graham and Van Der Eb, *Virology,* 52:456–467, 1973.
Graham et al., *J. Gen. Virol.,* 36:59–72, 1977.
Grunhaus and Horwitz, *Seminar in Virology,* 3:237–252, 1992.
Harland and Weintraub, *J. Cell Biol.,* 101:1094–1099, 1985.
Hattori et al., *Brain Res.* 170, 71 1979
Henry, et al., *J. Exp. Biol.* 196, 251 1994.
Hermonat and Muzycska, *Proc Natl Acad Sci USA.* 81(20): 6466–70, 1984
Hersdorffer et al., *DNA Cell Biol.,* 9:713–723, 1990.
Herz and Gerard, *Proc. Natl. Acad. Sci. USA,* 90:2812–2816, 1993.
Horellou et al., *Neuron* 5:393–402, 1990
Horwich et al., *J. Virol.,* 64:642–650, 1990.
Hoshimaru et al., *Proc. Natl. Acad. Sci. USA* 93, 1518 1996
Howell et al., *FEBS Lett.* 338(1):16–22, 1994
Ichinose et al., *Nat. Genet.* 8, 236 1994
Joki, et al., *Human Gene Ther.,* 6:1507–1513, 1995.
Jones and Shenk, *Cell,* 13:181–188, 1978.
Juncos, et al., *Neurology* 37:1742, 1987
Kageyama, et al., *J. Biol. Chem.,* 262(5):2345–2351, 1987.
Kaneda et al., *Science,* 243:375–378, 1989.
Kang et al., *J. Neurosci.* 13, 5203 1993.
Kaplitt, et al., *Nat. Genet.,* 8: 148–153, 1994.
Kaplitt, et al., *Arm. Thor. Surg.,* 62:1669–1676, 1996.
Karlsson et al., *EMBO J.,* 5:2377–2385, 1986.
Kato et al., *J. Biol. Chem.,* 266:3361–3364, 1991.
Kessler, et al., *Proc. Natl. Acad. Sci. USA,* 93:14082–14087, 1996.
Klein et al., *Nature,* 327:70–73, 1987.
Koeberl, et al., *Proc. Natl. Acad. Sci. USA,* 94:1426–1431, 1997.
Le Gal La Salle et al., *Science,* 259:988–990, 1993.
Levrero et al., *Gene,* 101:195–202, 1991.
Lindvall et al., *Ann. Neurol.* 35, 172 1994.
Lindvall et al., Science 247:574–577, 1990
Lindvall et al., *Ann. Neurol.* 22:457–468, 1987
Liu, et al., *Cell* 70, 539 1992
Macejak and Sarnow, *Nature,* 353:90–94, 1991.
Mandel et al., *J Neurosci.* 18(11):4271–84, 1998
Mann et al., *Cell,* 33:153–159, 1983.
Markowitz et al., *J. Virol.,* 62:1120–1124, 1988.
Marsden and Parkes, *Lancet* i, 345 1977
Marsden, *Trends Neurosci.* 9:512, 1986
McCown, et al., *Brain Res.,* 713:99–107, 1996.
McGurk et al., *Neuroscience.* 50(1):129–35, 1992
Mercer et al., *Experientia* 35, 101 1979
Merickel et al., *J. Biol. Chem.* 270, 25798 1995.
Misawa et al., *J. Neurochem.* 62, 465 1994.
Mizukami et al., *Virology,* 217:124–130, 1996.
Mouradian et al., *Ann. Neurol.* 27, 18 1990
Mulligan, *Science,* 260:926–932, 1993.
Myers, EPO 0273085
Neff and Hadjiconstantinou, *Prog. Brain Res.* 106, 91, 1995.
Nicolas and Rubenstein, In: *Vectors: A survey of molecular cloning vectors and their uses.* Rodriguez and Denhardt (eds.), Stoneham: Butterworth, pp. 494–513, 1988.
Nicolau and Sene, *Biochem. Biophys. Acta,* 721:185–190, 1982.
Nicolau el al., *Methods Enzymol.,* 149:157–176, 1987.
Nirenberg et al., *J. Neurosci.* 16, 4135 1996.
Nutt and Holford, *Ann. Neurol.* 39, 561 1996.
Nutt et al., *Arch. Neurol.* 49, 1123 1992
Nygaard et al., *Ann. Neurol.* 32, 603 1992
Olivierio, et al., *EMBO J.,* 6(7):1905–1912, 1987.
Olsson et al., *J. Neurosci.* 15, 3863 1995
Palmer et al., *Proc. Natl. Acad. Sci.* 88:1330–1334, 1991.
Papa et al., *Brain Res.* 662, 69 1994
Paskind et al., *Virology,* 67:242–248, 1975.
Pelletier and Sonenberg, *Nature,* 334:320–325, 1988.
Peppe et al., *Adv. Neurol.* 60, 698 1993.
Perales et al., *Proc. Natl: Acad. Sci.,* 91:4086–4090, 1994.
Peter et al., *Genomics,* 18(3):720–3, 1993
Peter et al., *J Biol Chem.* 269(10):7231–7, 1994
Phillips, *Neuroscience* 7, 1595–1609, 1982
Phizicky and Fields, *Microbiol Rev.* 59(1):94–123, 1995
Ping et al., *Microcirculation,* 3:225–228, 1996.
Poli and Cortese, *Proc. Natl. Acad. Sci. USA,* 86:8202–8206, 1989.
Ponnazhagan, et al., *J. Virol.,* 71:,1997b.
Ponnazhagan, et al., *Gene,* 190:203–210, 1997c.
Ponnazhagan, et al., *J. Virol.,* 71:3098–3104, 1997d.

Ponnazhagan et al., *Hum. Gene Ther.*, 8:275–284, 1997a.
Potter et al., *Proc. Nat'l Acad. Sci. USA*, 81:7161–7165, 1984.
Prowse and Baumann, *Mol Cell Biol*, 8(1):42–51, 1988.
Racher et al., *Biotechnology Techniques*, 9:169–174, 1995.
Ragot el al., *Nature*, 361:647–650, 1993.
Renan, *Radiother. Oncol.*, 19:197–218, 1990.
Rich et al., *Hum. Gene Ther.*, 4:461–476, 1993.
Ridgeway, In. Rodriguez R L, Denhardt D T, ed. Vectors: A survey of molecular cloning vectors and their uses. Stoneham: Butterworth, pp.467–492, 1988.
Rippe et al., *Mol. Cell Biol.*, 10:689–695, 1990.
Ron, et al., *Mol. Cell. Biol.*, 2887–2895, 1991.
Rosenfeld et al., *Science*, 252:431–434, 1991.
Rosenfeld et al., *Cell*, 68:143–155, 1992.
Roux et al., *Proc. Nat'l Acad. Sci. USA*, 86:9079–9083, 1989.
Ruppert et al., *J. Neurochem.* 61, 768 1993
Samulski et al., *EMBO J.*, 10:3941–3950, 1991.
Sawle et al., *Ann. Neurol.* 31, 166 1992.
Scherman and Boschi, *Neuroscience* 27, 1029–1035, 1988
Seiger, in *Neural Grafting in the Mammalian CNS*, Bjorklund and Stenevi, eds., Ch. 8, pp. 71–77 1985
Shoulson et al., *Neurology* 25, 1144 1975
Silva and Bunney, *Eur. J. Pharmacol.* 149, 307–315, 1988
Snow et al., *Ann. Neurol.* 34, 733 1993;
Stenevi et al., in *Neural Grafting in the Mammalian CNS*, Bjorklund and Stenevi, eds., Ch. 5, pp. 41–50, 1985
Stratford-Perricaudet and Perricaudet, In: *Human Gene Transfer*, Eds, O. Cohen-Haguenauer and M. Boiron, Editions John Libbey Eurotext, France, pp. 51–61, 1991.
Stratford-Perricaudet et al., *Hum. Gene Ther.*, 1:241–256, 1990.
Sulzer et al., *Mol. Pharmacol.* 49, 338 1996.
Surratt et al., *FEBS Lett.* 318, 325–330, 1993
Temin, In: *Gene Transfer*, Kucherlapati (ed.), New York: Plenum Press, pp. 149–188, 1986.
Toneguzzo et al., *Molec. Cell. Biol.* 6:703–706, 1986.
Top et al., *J. Infect. Dis.*, 124:155–160, 1971.
Tur-Kaspa et al., *Mol. Cell Biol.*, 6:716–718, 1986.
Turjanski, et al., *Neurology* 43, 1563 1993.
U.S. Pat. No. 4,419,446
U.S. Pat. No. 4,663,349
U.S. Pat. No. 4,663,349
U.S. Pat. No. 4,758,571
U.S. Pat. No. 4,771,073
U.S. Pat. No. 4,771,073
U.S. Pat. No. 4,826,875
U.S. Pat. No. 4,826,875
U.S. Pat. No. 4,863,962
U.S. Pat. No. 4,873,263
U.S. Pat. No. 4,873,263
U.S. Pat. No. 4,970,200
U.S. Pat. No. 5,607,969
U.S. Pat. No. 5,017,607
U.S. Pat. No. 5,017,607
U.S. Pat. No. 5,112,861
U.S. Pat. No. 5,135,956
U.S. Pat. No. 5,206,226
U.S. Pat. No. 5,210,076
U.S. Pat. No. 5,565,460
U.S. Pat. No. 5,576,353
U.S. Pat. No. 5,587,378
U.S. Pat. No. 5,607,969
U.S. Pat. No. 5,624,820
U.S. Pat. No. 5,650,443
U.S. Pat. No. 5,658,900
U.S. Pat. No. 5,674,703
U.S. Pat. No. 5,674,885
U.S. Pat. No. 5,677,344
U.S. Pat. No. 5,686,423
U.S. Pat. No. 5,703,100
U.S. Pat. No. 5,712,270
U.S. Pat. No. 5,756,548
U.S. Pat. No. 5,756,550
U.S. Pat. No. 5,807,871
U.S. Pat. No. 5,817,491
U.S. Pat. No. 5,817,690
U.S. Pat. No. 5,817,699
Ungerstedt et al., *Neurosci Res.* 5(0):73–96, 1973.
Ungerstedt et al., *Eur J Pharmacol.*, 21(2):230–7, 1973.
Varmus et al., *Cell*, 25:23–36, 1981.
Varoqui and Erickson, *Mol Neurobiol.* 15(2):165–91, 1997
Vinken et al., in Handbook of Clinical Neurology p. 185, Elsevier, Amsterdam, 1986 von Grafenstein et al., *FEBS Lett.* 298, 118 1992
Wachtel et al., *J. Neurochem.* 69, 2055 1997.
Wagner et al., *Proc. Natl. Acad. Sci.*, 87(9):3410–3414, 1990.
Walther and Stein, *J. Mol. Med*, Vol. 74: pp. 379–392. 1996
Weihe et al., *J. Mol. Neuroscien.*, 5, 149–164, 1994
Weiss et al., RNA Tumor viruses, 2nd Ed., Weiss et al., eds., Cold Spring Harbor Press, New York, 1985
Wictorin et al., *Nature*, 347:556–558, 1990
Wilson et al:, *Mol Cell Biol.* 10(12):6181–91, 1990.
Wolff et al., *Proc. Natl. Acad. Sci. USA* 86:9011–9014, 1987
Wong et al., *Gene*, 10:87–94, 1980.
Wu & Wu, *Biochemistry*, 27:887–892, 1988.
Wu & Wu, *J. Biol. Chem.*, 262:4429–4432, 1987.
Wu and Wu, *Adv. Drug Delivery Rev.*, 12:159–167, 1993.
Xiao, et al., *J. Virol.*, 70:8098–8108, 1996.
Yang et al., *Proc. Natl. Acad. Sci USA*, 87:9568–9572, 1990.
Zechner, et al., *Mol. Cell. Biol.*, 2394–2401, 1988.
Zelenin et al., *FEBS Lett.*, 280:94–96, 1991.
Zhu and Juorio, *Gen. Pharmacol* 26, 681 1995

What is claimed is:

1. A method for increasing dopamine levels in a mammal, said method comprising:

(a) obtaining cells from the mammal;

(b) transforming said cells with a first polynucleotide encoding L-amino acid decarboxylase (AADC) and a second polynucleotide encoding vesicular monoamine transporter (VMAT) under conditions suitable for the expression of AADC and VMAT, wherein said polynucleotides each are under the transcriptional control of a promoter; and (c) implanting said transformed cells into said mammal; whereby AADC converts L-DOPA in vivo to dopamine and VMAT sequesters said dopamine in endosomes of said cells, which sequestered dopamine releases over a longer duration of time than from cells without storage of L-DOPA.

2. A method of treating Parkinson's disease in a human subject comprising:

(a) obtaining cells from said subject;

(b) transforming said cells with a first polynucleotide encoding L-amino acid decarboxylase (AADC) and a second polynucleotide encoding vesicular monoamine transporter (VMAT) under conditions suitable for the expression of AADC and VMAT, wherein said polynucleotides are under the transcriptional control of a promoter;

(c) implanting said transformed cells into said subject; and (d) providing L-DOPA to said subject.

3. The method of claim 2, wherein said L-DOPA is administered orally, sublingually, subcutaneously, intravenously or by duodenal infusion.

4. The method of claim 2, wherein said L-DOPA is administered in a dose of between about 50 to about 2500 mg of L-DOPA per day.

5. The method of claim 4, further comprising administering carbidopa at a dose of between about 20 to about 300 mg carbidopa per day.

6. The method of claim 2, wherein said transformed cells are implanted via stereotaxic surgery.

* * * * *